US007790164B2

(12) United States Patent
Cao

(10) Patent No.: US 7,790,164 B2
(45) Date of Patent: Sep. 7, 2010

(54) FRAGMENTS OF ANTIBODIES TO EPIDERMAL GROWTH FACTOR RECEPTOR AND METHODS OF THEIR USE

(75) Inventor: Boliang Cao, Ada, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 29 days.

(21) Appl. No.: 11/940,322

(22) Filed: Nov. 14, 2007

(65) Prior Publication Data

US 2008/0131373 A1    Jun. 5, 2008

(51) Int. Cl.
*A61K 39/395* (2006.01)
*G01N 33/53* (2006.01)
*C07K 16/00* (2006.01)

(52) U.S. Cl. ............... 424/141.1; 424/130.1; 424/133.1; 424/143.1; 424/155.1; 424/178.1; 435/7.1; 435/7.2; 435/7.21; 435/7.23; 530/388.1; 530/387.1; 530/388.22

(58) Field of Classification Search ........................ None
See application file for complete search history.

(56) References Cited

OTHER PUBLICATIONS

Badache A, et al. A new therapeutic antibody masks ErB2 to its partners. Cancer Cell 5: pp. 299-301 (Apr. 2004).
Becerril B, et al. Toward selection of internalizing antibodies from phage libraries. Biochemical and Biophysical Research Communications 255: pp. 386-393 (1999).
Booth PJ. The trials and tribulations of membrane protein folding in vitro. Biochim Biophys Acta 1610: pp. 51-56 (2003).
Bruin R, et al. Selection of high-affinity phage antibodies from phage display libraries. Nature Biotechnology 17: pp. 397-399 (Apr. 1999).
Carbone DP. Epidermal growth factor receptor overexpression: the importance of context. Journal of Clinical Oncology 21, (No. 23): pp. 4268-4269 (Dec. 1, 2003).
Griffon-Etienne G, et al. Taxane-induced apoptosis decompresses blood vessels and lowers interstitial fluid pressure in solid tumors: clinical implications. Cancer Res 59: pp. 3776-3782 (Aug. 1, 1999).
Guillemard V, et al. Prodrug chmotherapeutics bypass p-glycoprotein resistance and kill tumors in vivo with high efficacy and target-dependent selectivity. Oncogene 23: pp. 3613-3621 (2004).
Guillemard V, et al. Taxane-Antibody Conjugates Afford Potent Cytotoxicity, Enhanced Solubility, and Tumor Target Selectivity. Cancer Res 61: pp. 694-699 (Jan. 15, 2001).
Holbro T, et al. ErbB receptors: Directing key signaling networks throughout life. Annu Rev Pharmacol Toxicol 44: pp. 195-217 (2004).
Holliger P, et al. Engineered antibody fragments and the rise of single domains. Nature Biotechnology 23 (No. 9): pp. 1126-1136 (Sep. 2005).
Jakobovits A, et al. Production of fully human antibodies by transgenic mice. Curr Opin Biotechnol 6: pp. 561-566 (1995).
Jiao Y, et al. Construction of human naive Fab library and characterization of anti-met Fab fragment generated from the library. Mol Biotechnol 31: pp. 41-54 (2005).
Jones PT, et al. Replacing the complimentary-determining regions in a human antibody with those from a mouse. Nature 321: pp. 522-525 (May 29, 1986).

Kohler G, et al. Continuous cultures of fused cells secreting antibody of predefined specificity. Nature 256: pp. 495-497 (Aug. 7, 1975).
Li S, et al. Structural basis for inhibition of the epidermal growth factor receptor by cetuximab. Cancer Cell 7: pp. 301-311 (Apr. 2005).
Liu C, et al. Design, synthesis, and bioactivities of steroid-linked taxol analogues as potential targeted drugs for prostate and breast cancer. J Nat Prod 67: pp. 152-159 (2004).
Mamot C, et al. Epidermal growth factor receptor-targeted immunoliposomes significantly enhance the efficacy of multiple anti-cancer drugs in vivo. Cancer Res 65 (No. 24): pp. 11631-11638 (Dec. 15, 2005).
Manning G, et al. The Protein Kinase Complement of the Human Genome. Science 298: pp. 1912-1934 (Dec. 6, 2002).
McCafferty J, et al. Phage antibodies: filamentous phage displaying antibody variable domains. Nature 348: pp. 552-554 (Dec. 6, 1990).
Molina MA, et al. Transtuzumab (herceptin), a humanized anti-Her2 receptor monoclonal antibody, inhibits basal and activated Her2 ectodomain cleavage in breast cancer cells. Cancer Res 61: pp. 4744-4749 (Jun. 15, 2001).
Nicholson RI, et al. EGFR and cancer prognosis. Eur J Cancer 37 (Suppl. 4): pp. S9-S15 (2001).
Ojima I, et al. Tumor-specific novel taxoid-monoclonal antibody conjugates. J Med Chem 45 (No. 26): pp. 5620-5623 (2002).
Raghava GP, et al. Method for determining the affinity of monoclonal antibody using non-competitive ELISA: a computer program. J Immunoassay 15 (No. 2): pp. 115-128 (1994).
Reichert JM, et al. Monoclonal antibody successes in the clinic. Nature Biotechnology 23 (No. 9): pp. 1073-1078 (Sep. 2005).
Salomon DS, et al. Epidermal growth factor-related peptides and their receptors in human malignancies. Crit Rev Oncol Hematol 19: pp. 183-204 (1995). *(25 part 1 includes pp. 183-204; 25 part 2 includes pp. 205-232).
Schlessinger J. Cell Signaling by Receptor Tyrosine Kinases. Cell 103: pp. 211-225 (Oct. 13, 2000).
Schrama D, et al. Antibody targeted drugs as cancer therapeutics. Nature Reviews of Drug Discovery 5: pp. 147-159 (Feb. 2006).
Souriau C, et al. Human antibody fragments specific for the epidermal growth factor receptor selected from large non-immunised phage display libraries. Growth Factor 22 (No. 3): pp. 185-194 (Sep. 2004).
Von Mehren M, et al. Monoclonal antibody therapy for cancer. Annu Rev Med 54: pp. 343-369 (2003).
Wang X, et al. In Vitro Efficacy of Immuno-Chemotherapy with Anti-EGFR Human Fab-Taxol Conjugate on A431 Epidermoid Carcinoma Cells. Cancer Biology & Therapy 6 (Issue 6): pp. e1-e7 (Jun. 2007).
Wu AM, et al. Arming antibodies: prospects and challenges for immunoconjugates. Nature Biotechnology 23 (No. 9): pp. 1137-1146 (Sep. 2005).
Yang XD, et al. Development of ABX-EGF, a fully human anti-EGF receptor monoclonal antibody, for cancer research. Crit Rev Oncol Hematol 38: pp. 17-23 (2001).
Yeung TK, et al. The mode of action of taxol: apoptosis at low concentration and necrosis at high concentration. Biochemical and Biophysical Research Communications 263 (No. 2): pp. 398-404 (1999).

*Primary Examiner*—Sheela J Huff
(74) *Attorney, Agent, or Firm*—Price, Heneveld, Cooper, DeWitt & Litton, LLP

(57) ABSTRACT

Antibody Fab fragments specific for the EGF receptor are disclosed, as are compositions and kits comprising these Fab proteins. The Fab proteins may be conjugated to drugs or other therapeutic agents or to diagnostic agents. Also disclosed are methods for diagnosing and treating diseases such as tumors and cancer in which cells express high levels of the EGFR, using the foregoing Fab molecules and conjugates.

42 Claims, 10 Drawing Sheets

A431 with Fab                A431 control

NIH 3T3 with Fab            NIH 3T3 control

FRAGMENTS OF ANTIBODIES TO EPIDERMAL GROWTH FACTOR RECEPTOR AND METHODS OF THEIR USE

FIELD OF THE INVENTION

This invention is in the field of molecular biology and medicine and, more specifically, relates to the EGF receptor.

BACKGROUND OF THE INVENTION

Upon binding an antigen, an antibody can mobilize the immune system to clear—molecules bearing the antigen and to kill antigen-bearing organisms or cancer cells. Beyond that, the antibodies can mimic the effect of native ligands with their receptors, activating or blocking the signaling pathways of the receptors. Moreover, antibodies are capable of targeting nucleic acids, chemotherapeutic agents, toxins or radionuclides that are bound to the antibodies to the surface of cancer cells when the antibodies recognize an antigen that serves as a specific tumor marker, thereby eliminating non-specific damage caused by these agents to normal cells (Schrama D, et al. *Nature Reviews of Drug Discovery* 5: 147-159 (2006)). Indeed, in addition to the conjugation of chemotherapeutics, radionuclides or toxins, antibody-targeted "drugs" are being developed in many fields, including antibody-cytokine fusion proteins for immune modulation, antibody-ligand fusion protein for apoptosis induction, and antibody directed enzyme pro-drugs for drug delivery. For the intracellular delivery of conjugated molecules, the antibody must be endocytosed by the target cell since an internalized antibody conjugate can promote accumulation of the conjugated agents. Some linkers involved in such conjugation also need to be internalized to release the compounds by the lysosome Schrama et al, supra). Because epidermal growth factor (EGFR) receptors are overexpressed on solid tumors, EGFR is an ideal target for antibody-directed drug delivery. Preferred forms of antibodies for this purpose are human anti-EGFR antibodies or antigen-binding fragments thereof.

Since the 1970s, rodent, particularly murine, antibodies have been widely applied for medical purposes, mainly for in vitro diagnosis (Kohler G, et al. *Nature* 256:495-7 (1975)). The first clinical study with therapeutic murine monoclonal antibodies (mAbs) was performed in the early 1980s, but failed due to (a) induction of human anti-mouse antibodies (HAMA), (b) short serum half-lives, and (c) low efficacy of interaction with human immune effector cells (Reichert J M, et al. *Nature Biotechnology* 23:1073-8 (2005)). Human antibodies are desired for treatment and in vivo diagnosis of human subjects in order to prevent the potential immune response that would eliminate non-human antibodies and thereby decrease their effects after the first use. The development of recombinant technology has enabled the generation of a chimeric antibodies that combine the variable region of a mouse antibody and the constant region of a human antibody) or fully human antibodies for clinical use. Currently, three kinds of technologies are used to create human antibodies in quantities sufficient for clinical use. Fully human antibodies may be produced by a transgenic mouse, humanization modification of mice antibodies, or by selection (by panning) of recombinant human antibody libraries (Jakobovits, A. *Curr Opin Biotechnol* 6: 561-6 (1995); Jones P T, et al. *Nature* 321: 522-5 (1986)).

Fifty nine (59) genes in the human genome encode 20 distinct families of receptor tyrosine kinases that regulate a great diversity of cellular processes including cell survival, proliferation and differentiation (Manning G, et al. *Science* 298: 1912-34 (2002); Schlessinger J. *Cell* 103:211-25 (2002)). The 170-kDa epidermal growth factor (EGF) receptor, (also known as HER 1 or ErbB-1), one of the best studied tyrosine kinase receptors, has long been related to malignant diseases. EGFR is over-expressed in human solid tumors, including non-small cell lung cancer, prostate cancer, breast cancer, gastric cancer and tumors of the head and neck, promotes tumorigenesis, angiogenesis and metastasis, and in some cases is related to prognosis of malignant disease as well as patients' response to chemotherapy (Salomon D S, et al. *Crit Rev Oncol Hematol* 19: 183-232 (1995); Carbone D P. *J Clin Oncol* 21: 4268-69 (2003); Nicholson R I, et al. *Eur J Cancer* 37 (Suppl 4): S9-15) (2001)). Given the critical role of EGFR in the survival of cancer cells, and the overexpression of EGFR as a transmembrane protein located on the cell surface, it has long been considered to be a practical target for tumor immunotherapy (Holbro T, et al. *Annu Rev Pharmacol Toxicol* 44: 195-217 (2004)).

The mechanism by which antibodies produce therapeutic outcomes include antibody dependent cellular cytotoxicity (ADCC), complement-mediated cytotoxicity, and the blocking of signal pathways that promote uncontrolled cell proliferation, e.g., with a neutralizing antibody (Von Mehren M, et al. *Annu Rev Med* 54:343-69 (2003)). In the case of the Erb family of EGFRs, antibodies have been developed to prevent heterodimerization of ErbB2 and ErbB3 (pertuzumab/Omnitarg™), to disrupt signal transduction (Trastuzumab/Herceptin™), and to prevent EGF binding to the EGFR (cetuximab/Erbitux™) (Molina M A, et al. *Cancer Res* 61:4744-49 (2001); Badache A, et al. *Cancer Cell* 5:299-301 (2004); Li S, et al. *Cancer Cell* 7:301-11 (2005)).

In addition, antibodies are good delivery vehicles for targeting agents to the EGFR for treatment or in vivo diagnosis. This can be done by conjugating chemotherapeutic drugs, radionuclides, or immunoliposomes for nanoscale delivery, and by directly fusing the antibody to an immunotoxin or cytokines using recombinant technology (Wu A M, et al. *Nature Biotech* 23:1137-46 (2005); Mamot C, et al. *Cancer Res* 65:11631-38 (2005)) Schrama D, et al., supra). An antibody-conjugated drug delivery system can direct toxic compounds to penetrate the targeted malignant tissue or cells specifically, thus decreasing the toxicity of drug to normal cells nearby and elsewhere, and increase the therapeutic effect by enhancing the accumulated dose of the drug in the targeted tissue. Conjugation also increases the solubility of some compounds in physiological solutions, enhancing the stability of the compounds, and preventing the conjugated drug from being pumped out of cells by the multidrug resistance associated p-glycoprotein transmembrane pump (Guillemard V, et al. *Cancer Res* 61: 694-9 (2001); Guillemard H, et al. *Oncogene* 23:3613-21 (2004)). Similarly, an antibody conjugated to a detectable label such as a radionuclide provides a method for early diagnosis of a malignancy, when a cell surface protein is overexpressed or mutated so that is distinguishable by an antibody from the unmutated form.

When using an antibody for drug delivery, internalization of the antibody is generally desired since it allows some compounds to be delivered intracellularly, for example after release, from the antibody. Schrama D, et al., supra Relatively smaller antibody fragments have higher penetrating speed into the solid tumor tissue (Holliger P, et al. *Nature Biotechnology* 23: 1126-36 (2005)), plus, if they are xenogeneic to the host, they have fewer foreign epitopes that can be recognized by the recipient's immune system. To avoid such immunogenic effects of xenoantibodies, most antibodies in clinical trials or use are human antibodies or at least chimeric (and humanized) antibodies so that they comprise a human constant regions linked to the original, xenogeneic (typically murine) variable regions.

Antibody phage display technology provides ways to raise a human antibody (McCafferty J, et al. *Nature* 348:552-4 (1990)). This technology allows rapid isolation of antigen-binding antibody fragments through the use of "bio-panning" and bypassing the immunization and fusion procedure the use of which would be unethical in humans. The bio-panning procedure, permits harvesting of antibodies or fragments with desired function by different panning strategies. A useful antibody to be subjected to immunoconjugation should bind, for example, to a cell surface molecule in its native condition. In the process of seeking a functional antibody which binds to a native antigen in a cell having a specific physiological condition, selection of the antibody/fragment on cells of a cell line that typify that physiological condition would enhance the chances of success. Bio panning on living cells using particular protocols could increase the probability of selecting an internalizing antibody (Becerril B, et al. *Biochem Biophys Res Comm* 255:386-93 (1999)).

SUMMARY OF THE INVENTION

The present invention provides an Fab fragment of an anti-EGFR mAb produced by bacteria (which strain is deposited in the American Type Culture Collection, 10801 University Blvd., Manassas, Va. 20110-2209, a recognized public depository for microorganisms, under Patent Deposit Designation ATCC PTA-7830, having been deposited on Aug. 22, 2006. The present invention further includes such an Fab fragment to which is conjugated an imaging agent or a drug. In one preferred embodiment, the conjugated drug is paclitaxel (TAXOL®).

An "anti-EGFR' mAb, Fab or other fragment or derivative described herein may also be referred to herein as an "EGFR mAb", "EGFR Fab', etc.

The present invention also includes an antigen-binding antibody fragment that binds to the same epitope or epitopes of EGFR as does the Fab fragment deposited in the ATCC as ATCC PTA-7830 with an affinity that is at least 10% of that of that Fab fragment. Such antibody fragment can be conjugated to a detectable label or imaging agent, or conjugated to a drug. In one embodiment the drug is paclitaxel.

A further embodiment of the present invention is an antibody Fab fragment that binds specifically to EGFR, characterized by an immunoglobulin heavy (H) chain portion of the Fab, which consists of a VH domain and a CH1 domain, and an immunoglobulin light (L) chain portion of the Fab, which consists of a VL domain and a CL domain, wherein the VL domain is SEQ ID NO:3 and the VH domain is SEQ ID NO:4; or a functional derivative of the Fab fragment that binds to EGFR with an affinity that is at least 10% of the affinity of the Fab fragment when measured in any antigen-binding assay, wherein said derivative is (i) a conservative amino acid substitution variant of the H or L chain of said Fab fragment, (ii) a deletion variant of said Fab fragment in which part or all of the CH1 or CL domain is deleted, or (iii) a deletion variant of said Fab fragment wherein the amino acid sequence of the L chain portion includes at least ten consecutive residues of VL SEQ ID NO:3 and the H chain portion includes at least ten consecutive residues of VH SEQ ID NO:4. Such Fab fragment or derivative can be conjugated to a detectable label or imaging agent, or to a drug. The can be a cancer chemotherapeutic drug, such as paclitaxel. Various embodiments of the invention of this paragraph can be formulate as a pharmaceutical or diagnostic composition.

The present invention also includes an isolated nucleic acid molecule encoding the antibody L chain of VL the Fab fragment of the preceding paragraph, and comprises SEQ ID NO:1 or a degenerate variant of SEQ ID NO:1 that encodes the amino acid sequence SEQ ID NO:3. Further, the present invention includes an isolated nucleic acid molecule encoding the antibody H chain VH of the novel Fab fragment, and comprises SEQ ID NO:2, or a degenerate variant of SEQ ID NO:2 that encodes the amino acid sequence SEQ ID NO:4. Another novel isolated nucleic acid molecule is a nucleotide sequence encoding the antibody L chain of the present Fab fragment which comprises (i) SEQ ID NO:1 or (ii) a degenerate variant of SEQ ID NO:1, linked to the antibody H chain of the present Fab fragment which comprises (iii) SEQ ID NO:2 or (iv) a degenerate variant of SEQ ID NO:2. Additional isolated nucleic acids include (a) the sequence of which is SEQ ID NO:1 or a degenerate variant of SEQ ID NO:1 that encodes amino acid sequence SEQ ID NO:3; or (b) the sequence of which is SEQ ID NO:2 or a degenerate variant of SEQ ID NO:2 that encodes amino acid sequence SEQ ID NO:4.

Also included within the scope of the invention are kits comprising the pharmaceutical or diagnostic composition of the present Fab fragment or a derivative thereof. The kit can further contain a least one additional reagent.

The present invention also includes a method for diagnosing EGFR-expressing tumor or cancer in a subject. In this method, the present Fab fragment or derivative conjugated to an imaging agent or detectable label is administered to a subject suspected of having an EGFR-expressing tumor or cancer. Detection of the imaging agent in or on cells or in a tissue is diagnostic of said tumor or cancer.

Another method of the present invention is detecting the presence of abnormal cells or tissues in a subject in which the amount or level of EGFR expression is abnormally high compared to a known control amount or level of EGFR in normal cells or tissues. This method includes: (a) administering to the subject the present anti-EGFR Fab fragment or derivative thereof; (b) measuring the binding of said Fab fragment to cells or tissue of the subject by measuring the amount or level of the label or imaging agent to determine the EGFR amount or level and (c) comparing the amount or level of EGFR measured in step (b) to said known control amount or level. In this method, a higher amount or level measured in step (b) compared to said normal amount or level is indicative of the presence of said abnormal cells or tissues in the subject. Further, an imaging agent, as described above, can be conjugated to the Fab fragment or derivative. In one embodiment, the abnormal cells are tumor or cancer cells or the abnormal tissue is tumor or cancer tissue.

Additionally, another use of the anti-EGFR Fab fragment or derivative thereof is in a method for enhancing the response of a subject with an EGFR-expressing tumor or cancer to a chemotherapeutic drug directed to the tumor or cancer. In this method, the Fab fragment or derivative thereof is administered to the subject an effective amount, and is (i) is internalized by cells of the tumor or cancer, and (ii) conjugated to said chemotherapeutic drug such that the binding of the drug-conjugated Fab fragment to the tumor or cancer cells results in internalization of the drug-conjugated Fab fragment, and leads to enhanced response of the subject to the drug as compared to administration of the drug alone.

CROSS-REFERENCE TO RELATED APPLICATION

Figure 1:
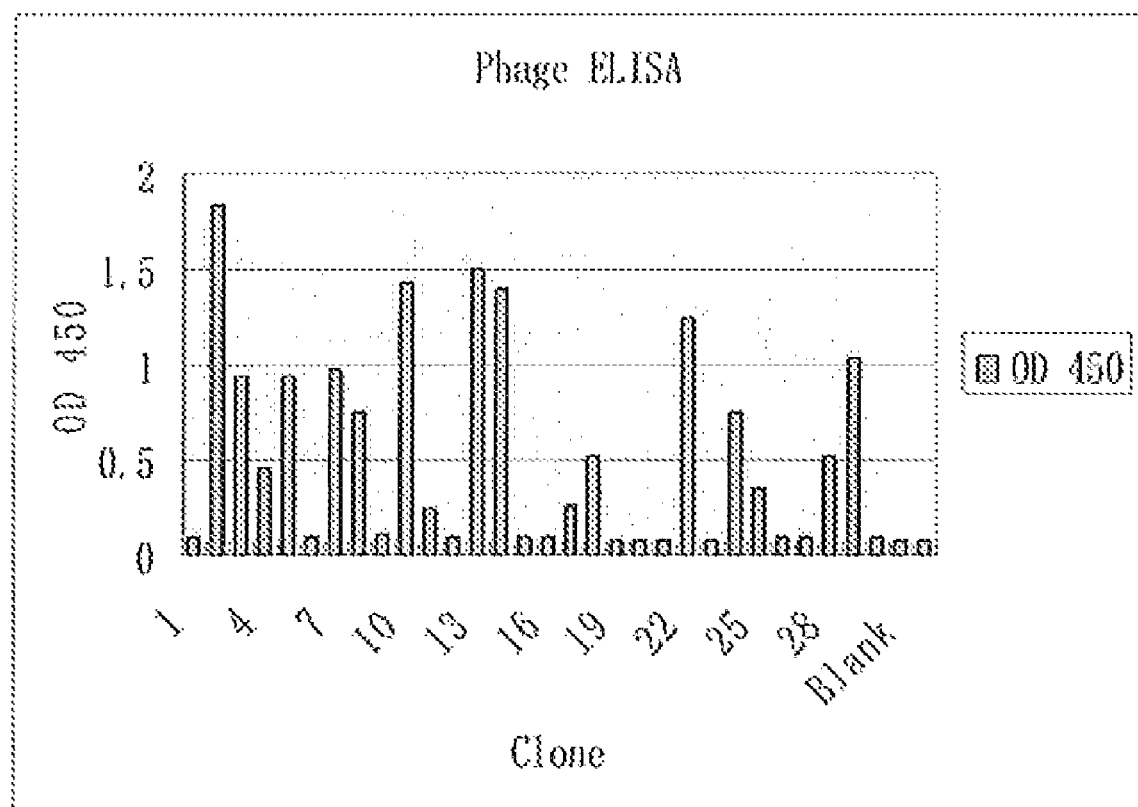
FIG. 1 is a graph showing binding specificity to EGFR of the antibody produced by 29 monoclones using phage ELISA.

This application claims the benefit of provisional application Ser. No. 60/865,739 filed Nov. 14, 2006, entitled EGFR FAB FRAGMENTS AND METHODS OF USE, the entire contents of which are incorporated herein in their entirety.

DETAILED DESCRIPTION OF THE PREFERRED EMBODIMENTS

The preferred embodiments of the present invention may be understood more readily by reference to the following detailed description of the specific embodiments and the Examples and Sequence Listing included hereafter. All references, patents, patent publications, articles, and databases, referred to in this application are incorporated-by-reference in their entirety, as if each were specifically and individually incorporated.

In accordance with the present invention there may be employed conventional molecular biology, microbiology, and recombinant DNA techniques within the skill of the art. Such techniques are explained fully in the literature, e g, Sambrook et al, "Molecular Cloning A Laboratory Manual" (1989), "Current Protocols in Molecular Biology" Volumes l-lll [Ausubel, R M, ed (1994)], "Cell Biology A Laboratory Handbook" Volumes l-lll [J E Cells, ed (1994))], "Current Protocols in Immunology" Volumes l-lll fCohgan, J E, ed (1994.

DEFINITIONS

The terms used herein have the meanings recognized and known to those of skill in the art, however, for convenience and completeness, particular terms and their meanings are set forth below.

As used in this specification and the appended claims, the singular forms "a", "an", and "the" include plural references unless the context clearly indicates otherwise.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see Example VII) (see also Freshney, Culture of Animal Cells: A Manual of Basic Technique (3rd ed. 1994)).

As used in herein "cell" is used in its usual biological sense, and does not refer to the entire multicellular organism. The cell can exist, for example, in vitro (e.g., in cell culture) or in a multicellular organism, including, e.g., birds, plants and mammals such as humans, cows, sheep, apes, monkeys, swine, dogs, cats, mice and rats. A cell can be prokaryotic (e.g., bacterial cell) or eukaryotic (e.g., an animal or plant cell).

"Nucleic acid" refers to deoxyribonucleotides or ribo-nucleotides and polymers thereof in either single- or double-stranded form. The term encompasses nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. Examples of such analogues include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses variants thereof (e.g., degenerate codon substitutions that encode the same amino acids) and complementary sequences, as well as the sequence explicitly indicated. The term "nucleic acid" is used interchangeably with gene, cDNA, mRNA, oligonucleotide, and polynucleotide.

The terms "polypeptide", "peptide," and "protein" are used interchangeably herein to refer to a polymer of amino acid residues. The terms apply to amino acid polymers in which one or more amino acid residue is an analogue or mimetic of a corresponding naturally occurring amino acid, as well as to polymers comprising naturally occurring amino acids.

The term "amino acid" includes naturally occurring and synthetic amino acids, as well as amino acid analogues and amino acid mimetics that function in a manner similar to naturally occurring amino acids. Naturally occurring amino acids are those encoded by the genetic code, as well as those amino acids that are later modified, e.g., hydroxyproline, alpha-carboxyglutamate, and O-phosphoserine. Amino acid analogues are compounds that have the same basic chemical structure as a naturally occurring amino acid, i.e., an α carbon that is bound to a hydrogen atom, a carboxyl group, an amino group, and, optionally, an R group (e.g., as in homoserine, norleucine, methionine sulfoxide, methionine methyl sulfonium). Such analogues have modified R groups (e.g., norleucine) or modified peptide backbones, but retain the same basic chemical structure as a naturally occurring amino acid. Amino acid mimetics aer chemical compounds that have a structure that is different from the general chemical structure of an amino acid, but that function in a similar manner.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservative modified variants" applies to both amino acid and nucleic acid sequences. With respect to particular nucleic acid sequences, a conservatively modified variant is a nucleic acid which encodes identical or essentially identical amino acid sequences, or for noncoding nucleic acids, to essentially identical sequences. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605 2608 (1985); Rossolini et al., Mol. Cell. Probes 8:91 98 (1994)). Because of the degeneracy of the genetic code, a large number of functionally identical nucleic acids encode any given protein. For instance, the codons GCA, GCC, GCG and GCU all encode alanine. Thus, at every position where an alanine is specified by a codon, the codon can be altered to any of the foregoing four codons without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a peptide, polypeptide, or protein sequence which alters, adds or deletes a single amino acid or a small percentage of amino acids in the sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the molecules of the present invention.

The following groups each contain amino acids that are conservative substitutions for one another: 1) Alanine (A), Glycine (G); 2) Serine (S), Threonine (T); 3) Aspartic acid (D), Glutamic acid (E); 4) Asparagine (N), Glutamine (Q); 5) Cysteine (C), Methionine (M); 6) Arginine (R), Lysine (K), Histidine (H); 7) Isoleucine (T), Leucine (L), Valine (V); and 8) Phenylalanine (F), Tyrosine (Y), Tryptophan (W). (see, e.g., Creighton, Proteins (1984)).

A "detectable moiety" or a "detectable label" is an atomic or molecular structure, in the present case, associated with, preferably bound to or conjugated with an Fab molecule of the present invention that is detectable by any means such as spectroscopic, photochemical, biochemical, immunochemical, or chemical means. For example, useful labels include radionuclides, fluorescent dyes, electron-dense reagents, enzymes (e.g., as commonly used in an ELISA), biotin, digoxigenin, haptens or proteins against which specific antibodies are available.

The terms "mutant," "modified," and "derivative" refer to the manipulation, of nucleic acid sequence or amino acid sequence encoding a protein, by recombinant or synthetic methods, resulting in a change in the nucleic acid sequence or amino acid sequence, respectively, such that the sequence is different from the original or unmanipulated sequence. For example, an nucleic acid sequence or amino acid sequence encoding a protein can be manipulated by extending, shortening, replacing, or otherwise changing the original or unmanipulated sequence, by using the recombinant or synthetic methods described herein or known to one of skill in the art.

The term "imaging" refers to a procedure or modality for generating an image of a detectable label or moiety in vivo, ex vivo, or in vitro, as described herein or known to one of skill in the art. Examples of imaging modalities include magnetic resonance, nuclear magnetic resonance, radioscintigraphy, positron emission tomography, computed tomography, near-infrared fluorescence, X-ray, ultrasound, ultraviolet light, or visible light, but are not limited thereto (for example, see Dahnhert, Radiology Review Manual, 4 th Edition, Lippincott, Williams & Wilkins (1999); Brant et al., Fundamentals of Diagnostic Radiobiology, 2 nd Edition, Lippincott, Williams & Wilkins (1999); Weissleder et al., Primer of Diagnostic Imaging, 2 nd Edition, Mosby-Year Book (1997); Buddinger et al., Medical Magnetic Resonance A Primer, Society of Magnetic Resonance, Inc. (1988); and Weissleder et al., Nature Biotech. 17: 375-378 (1999)).

By "therapeutically effective dose" or "diagnostically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

"Subject" or "patient" refers to a mammal, preferably a human, in need of treatment for a condition, disorder or disease.

In the present invention, the desired recombinant antigen-binding Fab fragment was isolated from a naïve phage display library targeting EGFR by panning on living cells and immobilized antigen by turns. These steps were followed by confirming binding to EGFR in a native state and compared to binding to the overexpressing EGFR tumor cell line, A431. The cancer drug paclitaxel was conjugated to the Fab, and the effect of the conjugate to free paclitaxel was investigated after demonstration of internalization ability. The apoptotic mechanism of action of the conjugate was also detected by the TUNEL assay.

Phage display is advantageous in that it is inexpensive and highly efficient. The time from bio-panning to obtaining the purified antibody is typically several weeks. Although the whole antibody can be generated by all of the above-described methods, smaller molecular weight Fab fragments or scFv constructs more efficiently penetrate into the tissue and cells at the targeting site compared to intact antibody molecules. This is especially true when the in cancer tissue with high tension. Thus, the present novel antigen-binding fragment targets the EGFR and is endocytosed.

The quality of bio-panning results relies on the diversity of the library, the preparation of the antigen and the strategies applied in the panning procedure. A library with higher diversity will have a greater likelihood for selection of high quality clones. The naïve library used here was constructed from the antibody repertoires of a non-immune individual and includes up to $10^9$ different clones. For the greatest possibility of capturing clones with high specificity and avidity to EGFR, the library was titrated and the density of phage adjusted to about $10^{13}$/ml before the first round of panning. This was the highest concentration of phage that could be so "condensed" while providing an average of $10^4$ copies of each clone. In addition, considering that number of acceptable clones should be under ten, the washing step in the first round was not stringent, leading to elution of about $10^6$ phages for amplification. This ensured that sufficient copies of each clone binding to EGFR was present for amplification. Fewer than $10^5$ elute phage could impede enrichment of specific phage. Becerril B, et al., supra.

The custom panning method used herein is based on a purified antigen coated in a solid phase, usually to a microtiter plate or a NUNC tube. However, receptors expressed on cell surfaces may be different from the purified protein passively bound to plastic because of conformational changes during purification and other processing steps, and could lead to failure of binding to protein with the native conformation (Booth P J. *Biochem Biophys Acta* 1610:51-6 (2003)).

So, in contrast to the regular panning procedure performed on the immobilized antigen, here, the regular panning method was combined with cell-based panning methods. This design was aimed to identify an antibody that bound to the extracellular domain of the EGFR. The A431 cell line was chosen to increase the chances of capturing the phage binding to the EGFR on the living cell. Specifically, the high level of expression of EGFR (up to $10^6$/cell) in A431 makes this cell line useful for selecting an anti human EGFR antibody or fragment. Indeed, the fully human anti-EGFR antibody ABX-EGF was generated by immunizing the XenoMouse $IgG_2$ strain with A431 cells (Yang X D, et al. *Crit. Rev Oncol Hematol* 38: 17-23 (2001)). Souriau et al. also reported isolation of a high affinity Fab with a Kd of $1.4 \times 10^{-8}$M by panning on A431 and two additional cell lines by turns starting from a naïve repertoire (Souriau C, et al. *Growth Factor* 22: 185-94 (2004)).

However, overexpressed EGFR molecules make up one part of the many cell surface molecules present on A431 or any other cells. To prevent selection and enrichment of non-specific phages that target molecules other than EGFR, a subtractive panning strategy was necessary to deplete the non-specific fragments from the repertoire. The phage was first mixed with NIH-3T3 cells. Even this step alone may be inadequate because differences other than EGFR overexpression must exist between NIH 3T3 and A431 cells. Therefore, a further panning step on immobilized EGFR protein was used to confirm the enrichment of phage that bind specifically to EGFR. Actually, Souriau et al. (supra) reported a failure to isolate anti-EGFR phage by a subtractive method when panning on EGFR-negative cells and A431 cells, so they used a second EGFR-positive cell line for further selection. As discovered by the present inventors, repeated panning on living cells and immobilized EGFR protein ensured enrichment of the EGFR-specific cell binding fragments. After seven rounds of panning, 17 of 30 randomly selected clones showed a positive result. Sequencing the seven phagemids giving the strongest binding signal by ELISA showed they were the same, indicating that a very high specific binding to EGFR was selected from the panel. Specific binding to both "native" EGFR and EGFR as it appears on the A431 cell surface was further confirmed by immunoprecipitation and FACS analysis after the Fab had been purified from the induced bacterial culture.

Several strategies help in creating internalizing antibodies, including inducing phage internalization under defined conditions. Strictly acid washes of the phage binding to the cell surface, followed by lysing the cell with triethylamine and rescue of the released phages from the cells. Here, trypsin digestion time was extended to thirty minutes to destroy the intact cell surface and elute thoroughly the phage that had bound to the cell surface. When selection was performed on the solid phase, the trypsin digestion time was also extended to thirty minutes. Bruin et al. reported modified elution protocols after failure to screen high affinity antibody on the solid phase (*Nature Biotechnology* 17: 397-9 (1999)). Here, a further freeze-thaw cycle was used to obtain internalized phages.

The Fab of the present invention was expressed in *E. coli* and purified A Hum-Zap internalization assay showed that the antibody fragment isolated from the library was internalized into A431 cells after binding the surface EGFR. In the Hum-Zap assay, an anti human Fab secondary antibody was conjugated with Saporin, a plant seed toxin that targets ribosomes and induces cell apoptosis after internalization. The cells treated with Hum-Zap, and primary Fabs that are not internalized can still survive.

The number of viable cells decreased with increased Hum-Zap concentration and Fab concentration, although neither Hum-Zap nor Fab alone affected cell viability, indicating internalization of the Fab. Also, a non-internalizing Fab did not suppress cell proliferation when combined with the Hum-Zap, showing that the internalization was triggered by the Fab, and not by native ligands. Although internalization of Fab after binding to the receptor can be investigated by other means (e.g., cell staining and confocal technology), the Hum-Zap made the analysis process simple. Moreover, the results showed that the Fab molecule of the present invention can be used for drug delivery.

After demonstrating the internalization of the EGFR Fab, the chemotherapeutic drug paclitaxel was conjugated to the EGFR Fab. Paclitaxel was first isolated from the bark of the Pacific yew tree (*Taxus brevifolia*)(Liu C, et al. *J Nat Prod* 67:152-9 (2004)0. Paclitaxel promotes microtubule polymerization, blocking the cells at the $G_2$-M phase of the cell cycle and leading to apoptotic death. More specifically, paclitaxel can induce apoptosis by stabilizing the spindle during mitosis at a very low concentration while inducing necrosis by stimulating the formation of microtubule bundles at a relatively high concentration in breast cancer cell lines 9Yeung T K, et al. *Biochem and Biophys Res Comm* 263:398-404 (1999)). More interestingly, paclitaxel has shown a clinical effect in combination with the therapeutic ErbB 2 antibody Herceptin by increasing the tumor vascular permeability to large molecules (Griffon-Etienne G, et al. *Cancer Res* 59:3776-82 (1999)). However, a non-discriminating side effect on normal tissue and multi drug resistance limits the efficacy of paclitaxel (Guillemard V, et al. *Cancer Res* 61: 694-99 (2001); Ojima I, et al. *J Med Chem* 45:5620-23 (2002).

EGFR was here selected as the tumor marker for antibody-directed drug delivery by the anti EGFR Fab. The $IC_{50}$ of A431 to paclitaxel is about 90 pM. Ojima I, et al. *J Med Chem* 45:5620-5623 (2002). At a very low concentration, which can not induce apoptosis of the A431 cells without paclitaxel conjugation, the viable cell number was profoundly decreased in a dose-effect manner. When checked under the microscope by a TUNEL assay, almost all of the cells underwent apoptosis even at a dose of 26 pM. This demonstrated the utility of the present novel human anti EGFR Fab for chemoimmunoconjugation therapy for solid tumors and for in vitro imaging diagnosis.

Thus, the expressed and purified Fab was shown to bind to EGFR in its native state and on the cell surface to trigger internalization. In vitro testing of the present Fab conjugated to paclitaxel, even at a very low doses, induced apoptosis in the tumor cell line A431 demonstrating the utility of this Fab for drug delivery and in vivo diagnosis, prognosis, and evaluation of chemotherapeutic responses.

All antibodies are immunoglobulin (Ig) molecules made up of two heavy (H) and two light (L) chains. Each H and L chain are linked by a disulfide bridge which is just N-terminal of a "hinge" region. Pairs of two chains, disulfide linked, include the same basic unit of four polypeptide chains: two light chains (L) and two heavy chains (H). Both the heavy chains and light chains have intra-chain disulfide bridges, which create polypeptide loops or domains, of about 110 amino acids. These domains are referred to as $V_H$ (variable domain of the H chain), $V_L$ (variable domain of the L chain), $C_H1$, $C_H2$, $C_H3$ (constant domains of the H chain), and $C_L$ (constant domain of the L chain). An Fab fragment was originally defined as is a papain digestion product of an intact antibody made of the N-terminal "half" of the H-chain which is now defined as $V_H$-$C_H1$ and all of the L-chain which is now defined as $V_L$-$C_L$ The Fab fragment contains the antigen binding site defined by the $V_H$ and $V_L$ domains of the H and L chains, respectively. Hence, the antigen binding site of any antibody (or antigen binding fragment thereof) is made up of the V domains ($V_H$ and $V_L$) that interact physically with one another. When physically associated, these domains together are also referred to as an Fv fragment, while recombinant forms of these domains in the form of a single chain are referred to as single chain Fv fragments (scFv).

The term "CDR" refers to the complementarity determining region or hypervariable region amino acid residues of an antibody which are responsible for antigen-binding. Framework or "FR" amino acid residues are those variable domain residues other than and bracketing the CDR regions. The variable (V) domain of an Ig chain includes hypervariable (HV) regions which are also known as complementarity-determining regions (CDRs) because they are important in "determining" the structure of the antibody combining site that is complementary the epitope bound. Each H and L chain V region has three HVs or CDRs. The segments on either side of each HV region which are relatively invariant are termed "framework regions" (FRs). Thus, the order of these regions in a V domain (from the N-terminus) is as follows: FR1-HV1-FR2-HV2-FR3-HV3-FR4. For example, the three HV regions are roughly from residues 28-35, 49-59 and 92-103, respectively. The framework regions form the β-sheets that provide the structural framework of the domain, with the HV sequences corresponding to three loops at one edge of each sheet that are juxtaposed in the folded protein. The HV loops from the VH and VL domains are brought together, creating a single HV site at the tip of the Fab fragment which forms the antigen binding site. (See, for example, Janeway, C. A., Jr. et al., IMMUNOBIOLOGY, 2n ed., Garland Publishing Inc., New York, 1996, chapter 3).

The present invention is directed to a novel anti-EGFR antibody fragment derived from a phage display library as described herein. See, also, Jiao Y, et al. *Mol Biotechnol* 31:41-54 (2005) for a detailed description of the general strategy for making these constructs. The DNA sequence encoding the $V_L$ region of the Fab has the sequence SEQ ID NO:1. The DNA sequence encoding the $V_H$ region of the Fab has the sequence SEQ ID NO:2.

The amino acid sequence of the $V_L$ region of the anti-EGFR Fab is preferably SEQ ID NO: 3; and the amino acid sequence of the $V_H$ region is preferably SEQ ID NO: 4. Such Fab fragment is encoded by the DNA of, and produced by, *E coli* bacteria deposited in the American Type Culture Collection under Patent Deposit Designation ATCC PTA-7830. This Fab fragment binds to an epitope (or epitopes) of EGFR.

The present invention also includes additional EGFR-binding antibody fragments that bind to the same epitope (or epitopes) with a binding affinity similar to that of the Fab fragment produced by the bacteria deposited as ATCC PTA-7830. Such similar binding affinity is at least about 1%, more preferably, at least about 10%, or 20%, or 30%, or 40%, or 50%, or 60%, or 70%, or 80%, or 90% of the affinity with which the Fab produced by the bacteria deposited as ATCC PTA-7830, or Fab that comprises SEQ ID NO:3 and SEQ ID NO:4 as its V region, binds to EGFR. It will be understood by those skilled in the art that the requisite affinity of these other EGFR-binding antibody fragments is such that the Fab can be used to carry out the described functions of the molecule, namely, binding to EGFRs on cells, preferably tumor or cancer cells and internalization by the cells, so that they deliver (a) labeled or detectable agents to the cells for diagnosis and prognosis or (b) drugs for therapy, such as a cytotoxic drug, e.g., paclitaxel, to kill the cells more effectively than the free drug that is not conjugated to the Fab (or derivative).

Binding affinity can be measured by any appropriate antigen-binding assay, e.g., the assay described in Example 5 herein. The affinity an antibody for an antigen can be determined experimentally using any suitable method (See, for example, Berzofsky et al., "Antibody-Antigen Interactions," In: FUNDAMENTAL IMMUNOLOGY, Paul, W E, Ed, Raven Press New York, N.Y. (1984), Kuby, J., IMMUNOLOGY, W H Freeman and Co New York, N.Y. (1992), and methods described herein). The measured affinity of a particular antibody-antigen interaction can vary depending on conditions of measurement (e.g., salt concentration, pH). Thus, measurements of affinity and other antigen-binding parameters (e.g., $K_D$, $IC_{50}$) are preferably made using standardized solutions and buffers such as described herein The present invention also includes functional derivatives of the EGFR Fab described above that bind to EGFR with an affinity similar to the binding affinity of the Fab. These functional derivatives bind to EGFR with at least about 1%, more preferably, at least about 10%, or 20%, or 30%, or 40%, or 50%, or 60%, or 70%, or 80%, or 90% of the affinity with which the anti-EGFR Fab described herein binds to EGFR. It will be understood by a person of skill in the art that the requisite affinity of the derivative should be such that the derivative possess the same activities and utilities as the Fab molecule as discussed above.

Functional derivatives of the anti-EGFR Fab fragment described herein include those Fab fragments that bind to EGFR with an affinity that is similar to the affinity with which the anti-EGFR Fab described herein binds to EGFR when measured in any antigen-binding assay, as noted above; and which derivative is preferably (i) a conservative amino acid substitution variant of the H or L chain of said Fab fragment, (ii) a deletion variant of said Fab fragment in which part or all of the $C_H1$ or $C_L$ domain is deleted, or (iii) a deletion variant of said Fab fragment wherein the amino acid sequence of the L chain portion includes at least ten consecutive residues of SEQ ID NO:3 and the H chain portion includes at least ten consecutive residues of SEQ ID NO:4. Such Fab derivatives may be derived from the provided sequences using techniques well known in the art. Amino acid substitutions, deletions, or additions, can be made in either the FRs or in the CDRs. While changes in the framework regions are usually designed to improve stability and reduce immunogenicity of the antibody, changes in the CDRs are usually designed to increase affinity of the antibody for its target. Such affinity-increasing changes are typically determined empirically by altering the CDR region and testing the antibody Alterations can be made according to the methods described in Antibody Engineering, 2nd ed (1995), ed Borrebaeck, Oxford University Press. An exemplary method for making a $V_H$ domain that is an amino acid sequence variant of the $V_H$ domain of the Fab described herein, comprises a step of adding, deleting, substituting or inserting one or more amino acids in the $V_H$, optionally combining the $V_H$ domain with one or more $V_L$ domains, and testing the $V_H$ domain or $V_H/V_L$ combination or combinations for specific binding to EGFR, and/or internalization into EGFR-expressing cells, and (preferably) testing the ability of such antigen-binding domain to modulate one or more EGFR-associated activities. A similar approach would be used to create and test variants of the $V_L$ domain disclosed herein, whether used alone or combined with one or more $V_H$ domains.

In one embodiment such functional derivative is a deletion variant of the Fab fragment in which all or part of (a) the $C_H1$ or the $C_L$ domain is deleted or (b) the L chain includes at least 10 contiguous residues of SEQ ID NO 3 and H chain includes at least 10 contiguous residues of SEQ ID NO 4.

Further, a Fab fragment may have CDR sequences that differ insubstantially from those of the Fab fragment described herein. Insubstantial differences include minor amino acid changes, such as 1 or 2 substitutions out of any of 5-7 amino acids in the sequence of a CDR. An amino acid can be substituted by an amino acid having similar charge, hydrophobic, or stereochemical characteristics. Such substitutions would be within the skills of a person of ordinary skill in the art. More substantial changes could be made in structure framework regions (FRs) without adversely affecting the binding properties of the Fab fragment.

Single-chain analogues of Fv fragments (scFv) are comprised of $V_H$ and $V_L$ regions linked into a single polypeptide chain by a flexible linker peptide and are generated by antibody engineering methods involving obtaining the genes encoding $V_H$ and $V_L$ regions (here, SEQ ID NOs: 1 and 2). The sscFv is formed by linking the component V genes with an oligonucleotide that encodes an appropriately designed linker peptide, such as (Gly-Gly-Gly-Gly-Ser)$_3$ or equivalent linkers. The linker bridges the C-terminus of the first V region and N-terminus of the second, ordered as either $V_H$-linker-$V_L$ or $V_L$-linker-$V_H$.

In another embodiment of the present invention, the Fab fragment or derivative is coupled or conjugated to a detectable label or an imaging agent. There are many different detectable labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the antibodies used in the invention, or will be able to ascertain such, by routine experimentation. Diagnostically-labeled (e.g., radiolabeled) antibodies are effective.

Suitable detectable labels for diagnosis and imaging include radioactive, fluorescent, fluorogenic, chromogenic, or other chemical labels. Useful radiolabels, which are detected simply by gamma counter, scintillation counter, PET scanning or autoradiography include 3H, 124I, 125I, 131I, 35S and 14C. In addition, 131I is a useful therapeutic isotope (see below).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, Handbook of Fluorescent Probes and Research Chemicals, Sixth Ed., Molecular Probes, Eugene, Oreg., 1996). Fluorescein, fluorescein derivatives and fluorescein-like molecules such as Oregon Green and its derivatives, Rhodamine Green and Rhodol Green, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green. derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red. derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., Science 281:2013-2016 (1998), and quantum dots, e.g., zinc-sulfide-capped cadmium selenide (Chan, W. C. W. et al., Science 281:2016-2018 (1998)).

In yet another approach, the amino groups of the Fab fragment or derivative thereof are allowed to react with a reagent that yields a fluorescent product, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The Fab fragment or derivative thereof can also be labeled for detection using fluorescence-emitting metals such as 152Eu+, or others of the lanthanide series. These metals can be attached to the peptide using such metal chelating groups as diethylenetriaminepentaacetic acid (DTPA) or ethylenediamine-tetraacetic acid (EDTA). DTPA in anhydride form can readily modify the NH2-containing antibodies.

For in vivo diagnosis, radionuclides may be bound to the antibody either directly or indirectly using a chelating agent such as DTPA and EDTA. Examples of such radionuclides are 99Tc, 123I, 125I, 131I, 111In, 97Ru, 67Cu, 67Ga, 68Ga, 72As, 89Zr, 90Y and 201Tl.

Generally, the amount of labeled antibody needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

The Fab fragments and derivatives thereof can also be made detectable by coupling or conjugating them to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds which have, or result in, chromophores with high extinction coefficients.

In situ detection of the labeled Fab or derivative thereof may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay, which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140-200 keV range, which may be readily detected by conventional gamma cameras.

A preferred diagnostic method is radioimmunoscintigraphic analysis, which is preferably performed in a manner that results in serial total body gamma camera images and allows determination of regional activity by quantitative "region-of-interest" (ROI) analysis.

The diagnostically labeled Fabs or derivatives thereof may be incorporated into convenient dosage forms. Preferably, for diagnosis, the labeled antibodies are administered systemically, e.g., by injection or infusion. When used, injection or infusion may be by any known route, preferably intravenous injection or infusion, subcutaneous injection, intramuscular, intracranial or intrathecal injection or infusion, or intraperitoneal administration. Injectables can be prepared in conventional forms, either as solutions or suspensions, solid forms.

Radioimmunoscintigraphy is an important and attractive modality for experimental and clinical molecular imaging of cancer. Established methods for radiolabeling antibodies in suitable quantity and of appropriate quantity for scintigraphy are available, feasible, relatively inexpensive, and adaptable to virtually any antibody regardless of its epitopic specificity. New radiolabeling methods are continually emerging, and many laboratories are evaluating a wide range of antibody derivatives—from full-length chimeric and humanized molecules, to monomeric and multimeric antibody fragments, to immunoconjugates—as potentially superior imaging and therapeutic agents, with improved targeting selectivity and more favorable biological turnover kinetics (Program and Abstracts, Ninth Conference on Cancer Therapy with Antibodies and Immunoconjugates. 2002. Cancer Biotherapy & Radiopharmaceuticals 17:465-494).

Moreover, the reagents, supplies, and equipment required to perform radioimmunoscintigraphy in experimental animals and in humans are commonplace. For decades decommissioned or refurbished clinical gamma cameras have proven satisfactory for animal imaging applications, and they continue to do so. Modified or custom-built gamma cameras adapted for small animal imaging are becoming more widely available.

The major advantage of scintigraphy as a molecular imaging modality (not limited to imaging with antibodies) is that the acquired images are inherently quantitative. The physics of gamma radiation and the mathematical analysis of nuclear images, including corrections for photon attenuation and other artifacts, are well understood. In animal models as well as in human studies one can noninvasively and accurately measure net accumulation and some kinetic parameters of radiopharmaceutical interactions with target lesions, and the concurrent collection of even a small set of biological samples (e.g., blood and excreta) for direct counting combined with quantitative analysis of diagnostic images enables useful dosimetry estimates for therapeutic purposes.

Many different radiopharmaceuticals are available for imaging neoplasms. They range from classical agents such as sodium iodide (Na-131I, thallium chloride (201 TlCl), and gallium citrate (67Ga-citrate) to highly selective positron-emitting reporter gene detection systems (Vallabhajosula S (2001), In: Nuclear Oncology. I Khalkhali et al., eds. Lippincott Williams & Wilkins, Philadelphia, Pa. pp. 31-62; Iyer M et al. (2001) J Nucl Med 42, 96-105). Radiolabeled molecules that bind to specific cell surface components provide one successful approach to tumor imaging and therapy. Examples are OctreoScan for imaging and potentially treating neuroendocrine neoplasms, CEAScan and OncoScint for imaging colorectal and ovarian cancers, and Bexxar and Zevalin for detecting and treating certain lymphomas.

In another embodiment of the present invention, the Fab fragment or derivative is coupled or conjugated to a drug. For example, the Fab fragment or derivative is conjugated to a chemotherapeutic drug. Therapeutic compositions or methods for treating tumors and cancer may compriseone or more additional anti-tumor drugs or agents, such as mitotic inhibitors (e.g., vinblastine); alkylating agents (e.g., cyclophosphamide); folate inhibitors (e.g., methotrexate); antimetabolites (e.g., 5-fluorouracil and cytosine arabinoside); intercalating antibiotics (e.g., adriamycin and bleomycin); promoters of microtubule polymerization (e.g., paclitaxil) or enzyme inhibitors (e.g., topoisomerase inhibitors, such as etoposide). One preferred chemotherapeutic conjugate with the present Fab or derivative thereof is paclitaxil.

Another embodiment of the present invention is a pharmaceutical or diagnostic composition of the present Fab fragment or a derivative thereof. In said composition the Fab or derivative thereof is dissolved in a pharmaceutically acceptable carrier, preferably an aqueous carrier. A variety of aqueous carriers can be used, e.g., buffered saline and the like. These solutions are preferably sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies or Fab fragments, when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical compositions comprising a known cancer therapeutic in combination with the conjugates disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents, since tumor-bearing patients may also suffer from various infections or have diminished resistance to infections.

Also within the scope described herein are kits comprising the pharmaceutical or diagnostic composition of the present Fab fragment or a derivative thereof. The kit can further contain a least one additional reagent.

The present invention also includes a method for diagnosing EGFR-expressing tumor or cancer in a subject. In this method, the present Fab fragment or derivative conjugated to an imaging agent or detectable label is administered to a subject suspected of having an EGFR-expressing tumor or cancer. Detection of the imaging agent in or on cells or in a tissue is diagnostic of said tumor or cancer.

Another method of the present invention is detecting the presence of abnormal cells or tissues in a subject in which the amount or level of EGFR expression is abnormally high compared to a known control amount or level of EGFR in normal cells or tissues. This method includes: (a) administering to the subject the present anti-EGFR Fab fragment or derivative thereof; (b) measuring the binding of said Fab fragment to cells or tissue of the subject by measuring the amount or level of the label or imaging agent to determine the EGFR amount or level and (c) comparing the amount or level of EGFR measured in step (b) to said known control amount or level. In this method, a higher amount or level measured in step (b) compared to said normal amount or level is indicative of the presence of said abnormal cells or tissues in the subject. Further, an imaging agent, as described above, can be conjugated to the Fab fragment or derivative. In one embodiment, the abnormal cells are tumor or cancer cells or the abnormal tissue is tumor or cancer tissue.

Additionally, another use of the anti-EGFR Fab fragment or derivative thereof is in a method for enhancing the response of a subject with an EGFR-expressing tumor or cancer to a chemotherapeutic drug directed to said tumor or cancer. In this method, the Fab fragment or derivative thereof is administered to the subject an effective amount, and is (i) is internalized by cells of the tumor or cancer, and (ii) conjugated to said chemotherapeutic drug such that the binding of the drug-conjugated Fab fragment to the tumor or cancer cells results in internalization of the drug-conjugated Fab fragment, and leads to enhanced response of the subject to the drug as compared to administration of the drug alone.

Having now generally described the invention, the same will be more readily understood through reference to the following examples, which are provided by way of illustration, and are not intended to be limiting of the present invention, unless specified.

EXAMPLES

Example 1

Materials and Methods

Phage Library, Helper Phage and Bacterial Strain

A naïve Fab library was constructed on phagemid vector Pcomb3X from the Scripps Research Institute (La Jolla, Calif.) as described elsewhere (Jiao Y, et al. *Mol Biotechnol* 31:41-54 (2005)). Before the first round of panning, the library was titrated and $2 \times 10^{13}$ clones were collected. The VCSM 13 helper was purchased from Stratagene (Cat: #0450468). The *E. coli* strain XL-1-blue was also from Stratagene (Cat: #200158, Genotype: Δ(mcrA)183 Δ(mcrCB-hs-dSMR-mrr)173 endA1 supE44 thi-1 recA1 gyrA96 relA1 lac [F' proAB lacIqZΔM15 Tn10 (Tetr)]. Another *E. coli* strain Top 10 F' for expressing the Fab was from Invitrogen (Cat: #C3030-03, Genotype: F'{lacIq Tn10 (TetR)} mcrA Δ(mrr-hsdRMS-mcrBC) Φ80lacZΔM15 ΔlacX74 recA1 araD 139 Δ(ara-leu)7697 galU galK rpsL endA1 nupG). Both of these *E. coli* strains were tested to preclude contamination with wild type phage.

Cell Lines and Purified EGFR

Two cell lines were used for subtractive panning. NIH 3T3 cells were used to deplete the non-specific phage during panning procedure. The vulvar squamous carcinoma cell line A431, which expresses an average of about a $10^6$ EGFRs on the surface of each cell, was used to capture phage that bind to the native conformation of the EGFR. Both cell lines were grown in DMEM medium (Gibco, 11965-092) with 10% FBS, 1% P/S (Gibco, 15240-062). Full length EGFR molecules were affinity purified from the A431 cell lysate in RIPA lysis buffer (1% NP-40, 1% sodium deoxycholate, 1% SDS, 0.15M NaCl, 2 mM EDTA, 50 mM NaF in 10 mM phosphate buffer, pH 7.2). The eluted EGFR was verified by western blotting and quantified by BCA assay after being concentrated in phosphate buffered saline (PBS).

Bio-Panning Methods

To isolate phages that targeted EGFR on the cell surface, panning was performed by subtractive panning on living cells and on immobilized intact EGFR protein by turns. The $1^{st}$, $2^{nd}$, $3^{rd}$ and $6^{th}$ rounds of panning were performed on the cells. More than $10^6$ cells were used in each round. The cells were starved by incubation in medium lacking FBS for 12 hours, then washed in by PBS twice, detached from the flask using the by cell dissociation buffer (Gibco, 13151-014) at 37° C. for ten minutes, washed twice again with PBS. Then NIH 3T3 cells were resuspended in the presence of $10^{13}$ phagemids in 1 ml 1% BSA-PBS, shaken at 37° C. for 30 minutes, and centrifuged at 5000 g for 3 minutes. The supernatant was collected and used to resuspend the A431 cells, which were incubated again at 37° C. for 1 hour. Then the cells were washed in DMEM 1% BSA-PBS by turns to remove non-specifically bound phage as the wash times increased with the panning rounds, followed by treatment with 500 μl trypsin-EDTA (Gibco, 25300-054) at 37° C. for 30 minutes. Another 450% PBS, pH 7.4, was added to stop the trypsin reaction. Cell pellets were collected after centrifuging and resuspended in 500 μl PBS, frozen and thawed 5× in an ethanol-dry ice bath. The phage removed from cell surface by trypsin and released from inside the cells by freeze/thaw were collected together and used to infect *E. coli* XL-1-blue for amplification.

To exclude phage particles that had bound to A431 cell surface molecules other than EGFR, the 4$^{th}$, 5$^{th}$ and 7$^{th}$ rounds of panning were performed on the immobilized full length EGFR protein. The amount of coated EGFR protein was gradient-decreased in the three rounds. After blocking, about $10^{12}$ to $10^{13}$ phages were added to each well, incubated at 37° C. for 2 hours. The non-specific phagemids were washed out by 0.5% Tween-PBS, whereas bound phages were eluted by 1% trypsin-EDTA for 30 minutes at 37° C.

Specific Screening

After seven rounds of panning, twenty-nine monoclones were randomly grown to test the binding specificity of their antibody products to EGFR by phage ELISA. A ratio of 2.5 between absorbance ($OD_{450}$) versus blank tubes was chosen as the standard to select positive clones. As shown in FIG. 1, 17 out of the 30 clones were positive. The seven clones with the strongest binding were analyzed by coding sequence and were found to be identical.

Single clones from the *E. coli* XL-1-blue infected by the 7$^{th}$ round eluted phage were grown in 1 ml SB medium with 50 µg/ml carbenicillin, 1% glucose, with shaking at 37° C. separately until the early log period. $10^9$ VCSM13 helper phage were added to each culture which were incubated with shaking for another 2 hours, after which kanamycin (Gibco, 11815-024) was added to 70 µg/ml, then allowed to grow overnight. The 50 µl supernatant of each overnight culture was transferred to wells coated with 100 ng intact EGFR protein; the wells had been pre-blocked with freshly prepared 5% milk blocking buffer (5% milk, 0.5% tween-PBS) at 37° C. for 2 hours. After incubation at room temperature for 1 hour, the fluid in the wells was decanted. The plate was washed with 0.5% tween-PBS, and each well received 50 µl of a 1:4000 dilution of secondary antibody (HRP conjugated sheep anti M13 antibody; Amersham Biotech, Cat: #27-9421-01) in milk blocking buffer and was allowed to incubate for another hour and washed again. The HRP substrate solution TMB:$H_2O_2$=1:1 (Pierce (??), ImmunoPure TMB Substrate Kit Prod# 34021) was added and developed 30 minutes before stopping by 1M $H_2SO_4$. The absorbance value at 450 nm was read using a µQuant plate reader (Bio-Tek Instruments Inc.)

Expression and Purification of Soluble Antigen-Binding Fragments

Figure 2:
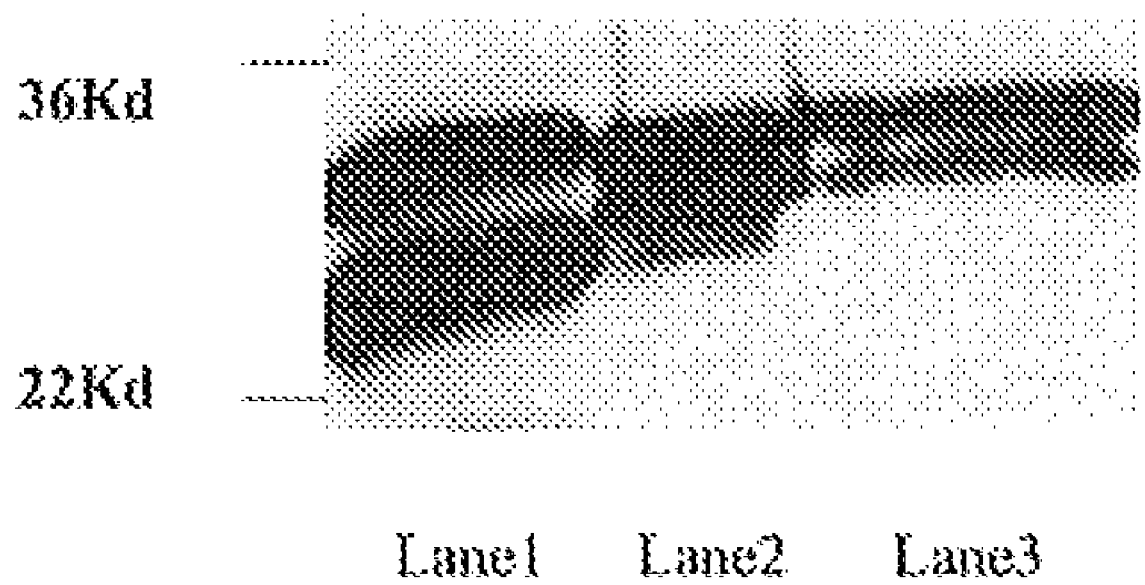
FIG. 2 is a Western blot confirming the expression of EGFR Fab.
Figure 3:
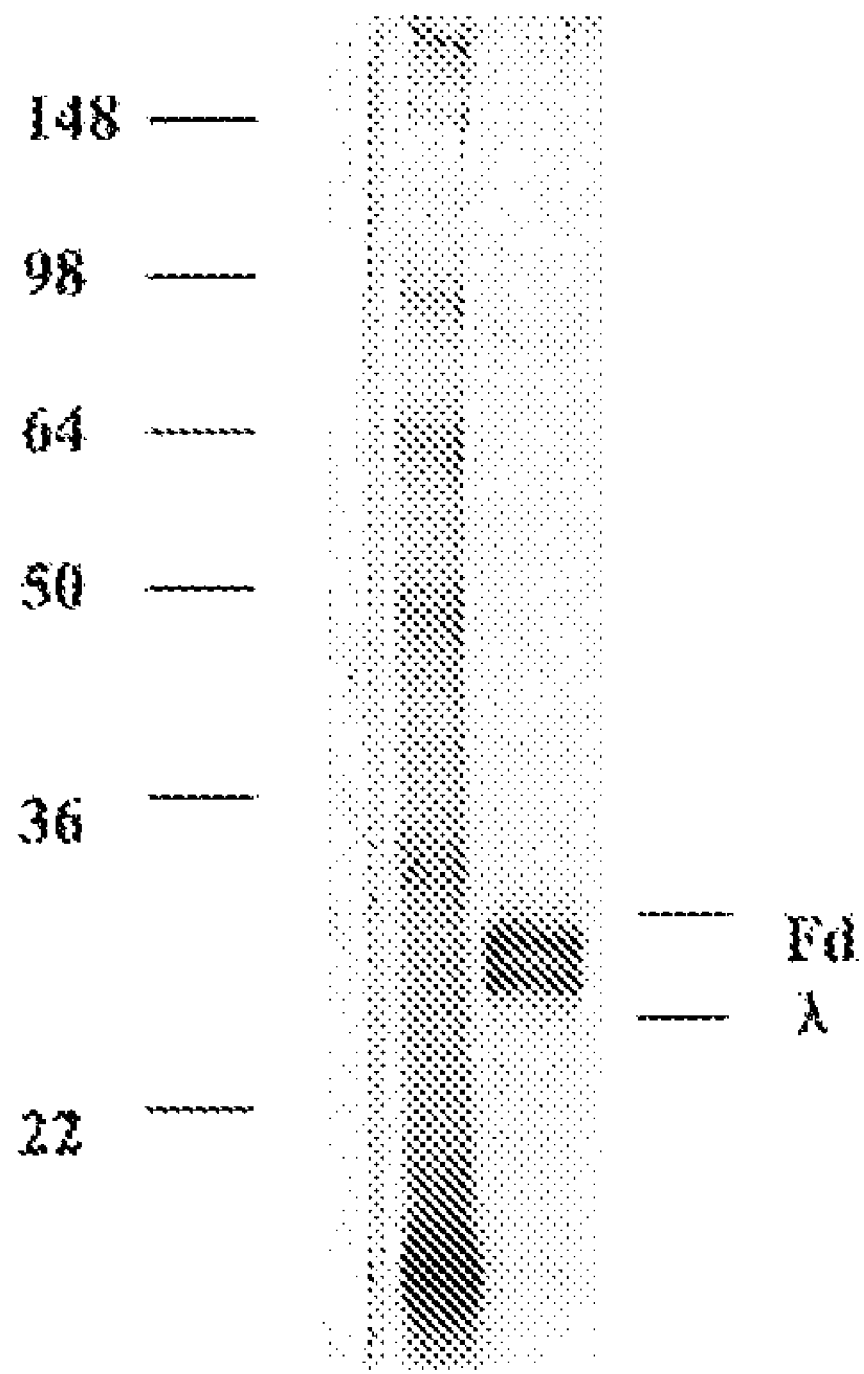
FIG. 3 shows results of Coomassie blue staining of purified EGFR Fab from a Q HP sepharose column.

The Fab antibody fragment was expressed not only in the periplasm but also secreted into the culture medium. After the two steps of purification, pure Fab was separated from other bacterial proteins (FIG. 2 and FIG. 3). In FIG. 2: Lane 1 is shown a positive control; Lane 2 is a bacterial lysate; and Lane 3 is culture medium.

The recombinant Fab was expressed in the *E. coli* Top 10 F. An overnight culture of a single clone was re-inoculated at a ratio of 1:30 in SB medium with 50 µg/ml carbenicillin until the $OD_{600}$ was about 1.0, after which the bacteria were induced by 1 mM IPTG (Research Products International, Prospect, Ill., Cat: #156000-5.0) in the presence of 4% sucrose at 22° C., and harvested 18 to 36 hours later. The soluble Fab was purified from periplasm of the bacteria by affinity purification followed by ion exchange chromatography.

Statistical Analysis

The data of the MTS were expressed as means±SD. The data were analyzed by one-way ANOVA, and differences in which $p<0.05$ were considered significant Example 2

Flow Cytometric Analysis

Fluorescence Activated Cell Sorting or "FACS'

Figure 5:
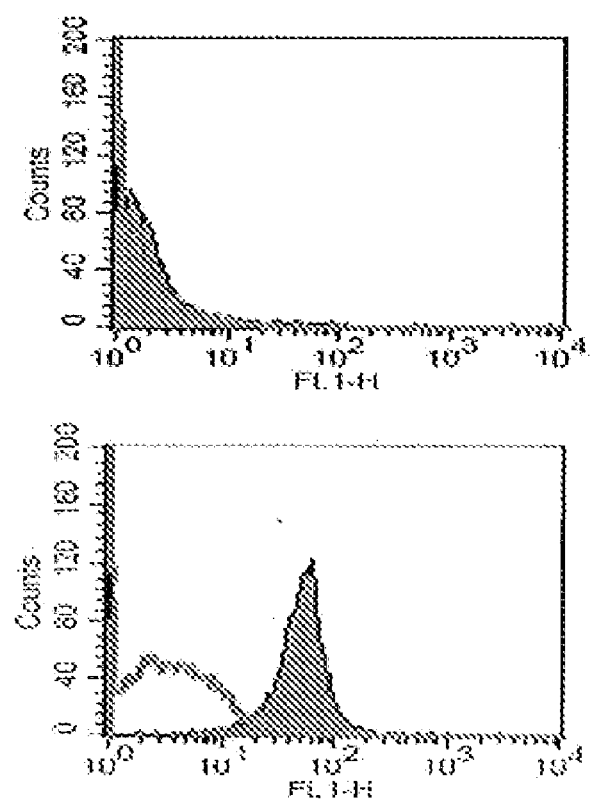
FIG. 5 is a graph showing binding of purified EGFR Fab to A431 cells analyzed by flow cytometry

After observing the binding of the Fab to native EGFR, the binding capacity of the Fab to the EGFR in living cells was further tested. FACS analysis demonstrated binding of Fab to cells of the A431 cell line (~$10^6$ human EGFR per cell) while no significant binding to murine NIH 3T3 fibroblasts was detected (FIG. 5). In FIG. 5: the upper graph shows an NIH-3T3 control, and lower graph shows the A431 cell line.

The NIH 3T3 and A431 cells were prepared as described for the panning procedure. The cells were incubated with 100 µg/ml Fab at 4° C. for 45 minutes after blocking with 1% BSA-PBS at 4° C. for 30 minutes. Cells were stained by incubation with a 1:25 dilution of FITC-labeled anti human Fab IgG (Sigma, F5512) at 4° C. for 20 minutes, followed by FACS analysis (using Cellquest software; Becton Dickinson Bioscience). The control group was cells incubated only with the secondary antibody.

Example 3

Immunoprecipitation

Figure 4:
FIG. 4 is a Western blot showing immunoprecipitation of EGFR by the EGFR Fab.
Figure 4:
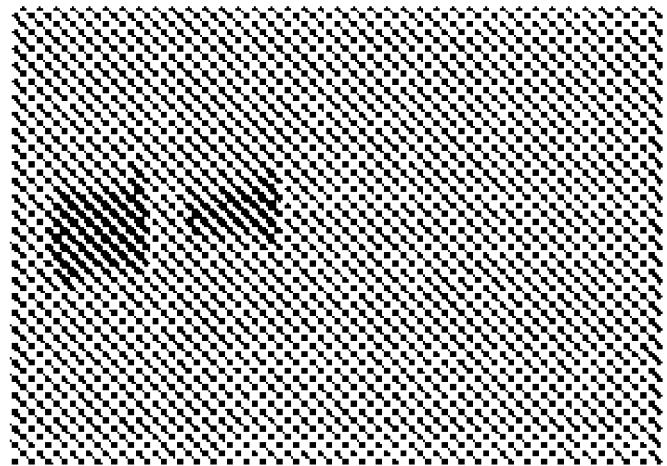

After purification, the binding capacity of the Fab to the EGFR (native conformation) was detected by immunoprecipitation. As shown in FIG. 4, the Fab bound native EGFR from an A431 lysate as detected by western-blotting with the further confirmation of the positive control. In FIG. 4, L1 is a positive control (A431 lysate Western blot); L2 is an immunoprecipitate (IP) of an A431 lysate; L3 is an NIH-3T3 cell immunoprecipitate; L4 is a negative control (Fab+RIPA buffer+Protein A beads). The Fab molecule did not precipitate any protein from the NIH3T3 cell lysate.

500 µl of lysate of each cell type (from about $5 \times 10^5$ cells) was mixed with 50 µg Fab, 100 µl Protein G Agrose beads (Invitrogen, 15920-010) and incubated overnight at 4° C. and. The next day, the beads were washed 3 times in 0.1% Tween-PBS and resuspended in 40 µl 2×SDS-"loading buffer", heated at 100° C. for 10 minutes, then centrifuged at 5,000 g for 5 minutes, and the supernatant collected for western-blotting to detect the precipitated EGFR.

Example 4

Staining

Figure 6:
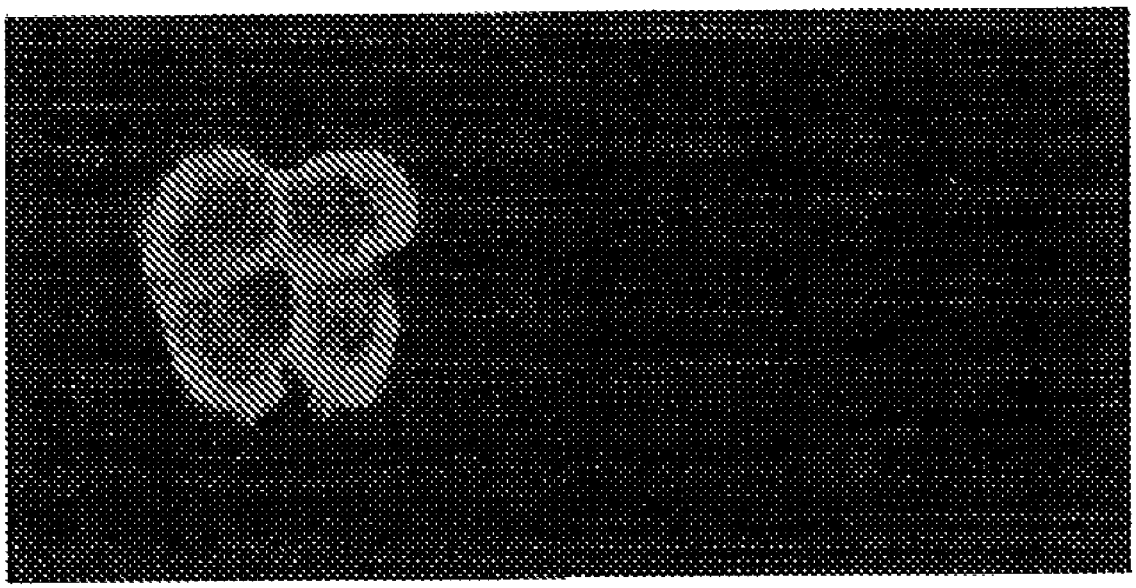
FIG. 6 is a micrograph showing binding of purified EGFR Fab to A431 cells visualized by fluorescence staining.
Figure 6:
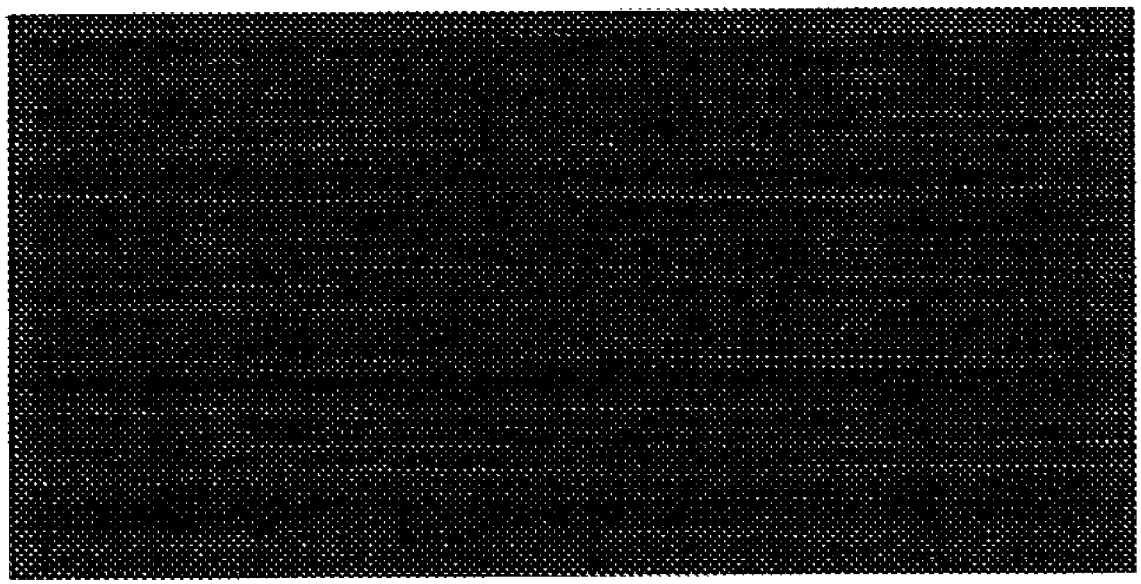

To provide morphological evidence of cell binding, a cell staining experiment was performed. The method of fixing by acetone/methanol, which did not modify the conformation of protein, proved that the Fab bound to cell surface EGFR in its native state. Cell binding was observed by fluorescence microscopy, (FIG. 6). (FIG. 6 is 200× enlarged)

A431 and NIH 3T3 cells were grown in slide chambers for staining. After reaching confluence, cells were fixed using a mixture of acetone/methanol, blocked with 5% milk-PBS at 37° C. for 1 hour, incubated with 33 µg/ml Fab at 37° C. for another hour before staining with a 1:1600 dilution of rhodamine labeled goat anti human Fab (Jackson Immuno Research Lab, cat#: 109-296-097) in the dark.

Example 5

Affinity Calculation

Figure 7:
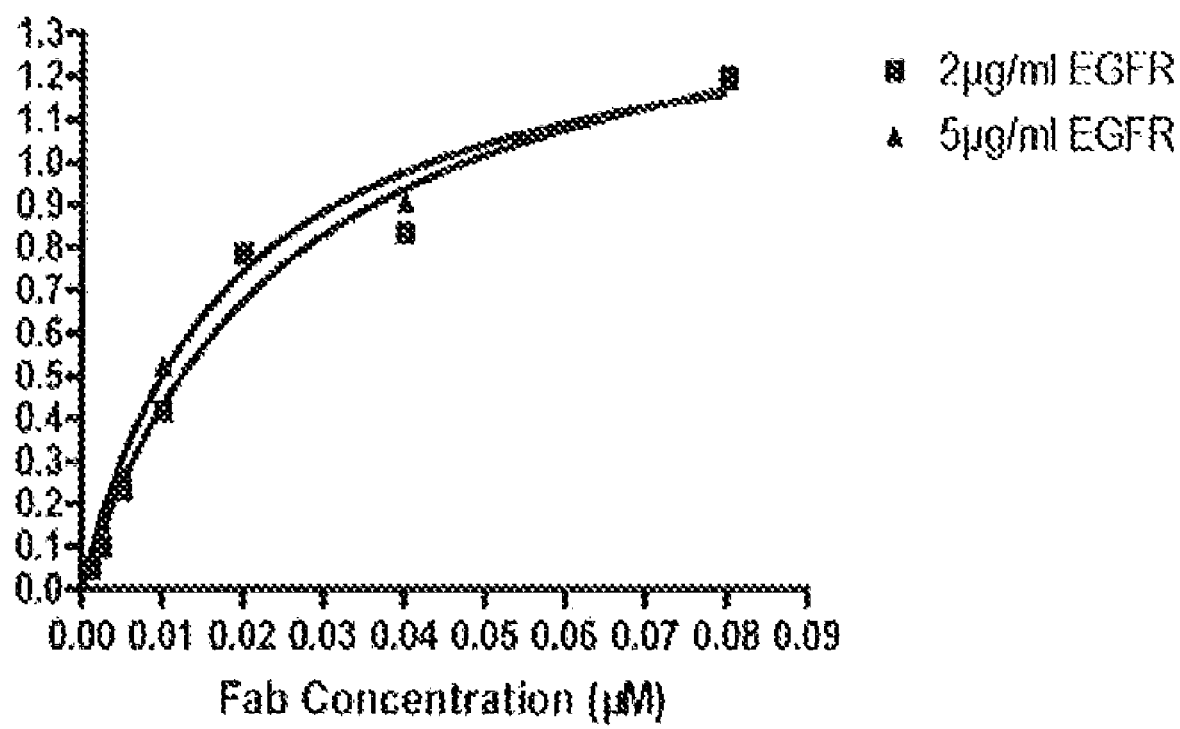
FIG. 7 is a graph showing binding affinity curves of non-competitive ELISA plotted by Graphpad Prism 4.

The non-competitive ELISA result using different antigen concentrations is shown in Table 1. The hyperbolic curves were plotted by Graphpad Prism (FIG. 7). Calculated from the curves, the plate coated with 2 μg/ml antigen gave an OD-50 at an Fab concentration of 0.02582 μM. The plate coated with 5 μg/ml antigen gave an OD-50 at an Fab concentration of 0.01842 μM. The affinity was calculated as an association constant ($K_{aff}$) as follows:

$$K_{aff}=1.5/(2.5\times0.02582-0.01842)=3.25\times10^7 M^{-1},$$

The dissociation constant Kd was $3.07\times10^{-8}$ M.

TABLE 1

Non-competitive ELISA

| Fab Concentration | Plate coated with 2 μg/ml antigen | Plate coated with 5 μg/ml antigen |
|---|---|---|
| 0.08 | 1.198 | 1.189 |
| 0.04 | 0.834 | 0.906 |
| 0.02 | 0.785 | 0.785 |
| 0.01 | 0.416 | 0.525 |
| 0.005 | 0.234 | 0.287 |
| 0.0025 | 0.1 | 0.156 |
| 0.00125 | 0.048 | 0.077 |

The affinity of the Fab was calculated by non-competitive ELISA as described elsewhere (Raghava G P, et al. *J Immunoassay* 15:115-28 (1994)). The EGFR proteins were immobilized to an ELISA plate at two different concentrations: 2 μg/ml and 5 μg/ml. After the plate was blocked by 5% milk-PBS, the serially diluted Fab was added to each well. The concentration of Fab and the absorbance optical at 450 nm were plotted in two hyperbolic curves and each Kd was calculated by Graphpad Prism Demo Version. The association constant ($Ka_{ff}$) was calculated by Kd={2.5×[Ag']−[Ag]}/1.5, where "[Ag']" is the free Fab concentration at OD-50 of 2 μg/ml coated antigen, while "[Ag]" is the free Fab concentration at OD-50 of 5 μg/ml coated EGFR.

Example 6

Internalization Assay

Figure 8:
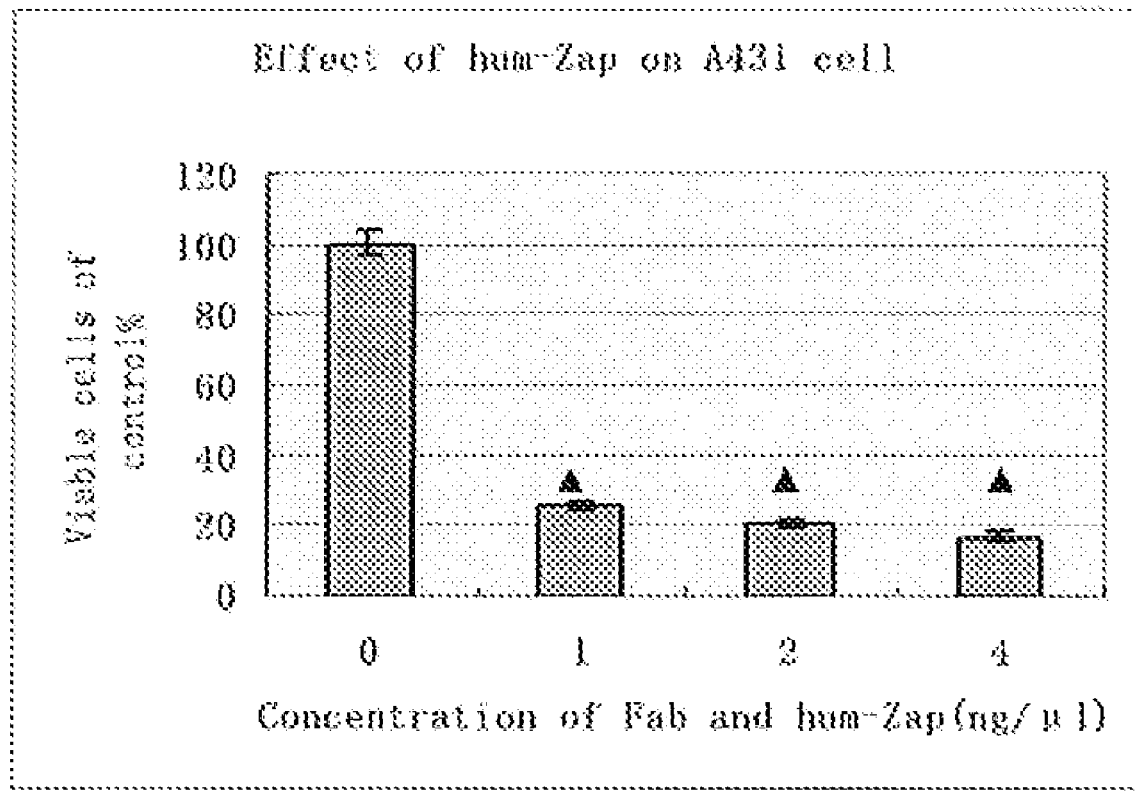
FIG. 8 is a graph showing the effect of different concentrations of hum-Zap with EGFR Fab on the A431 cells (▲): vs. untreated group (left-most bar).

Compared to negative controls (cells treated with Fab or hum-Zap only), proliferation of the Fab and hum-Zap co-treated cells' was clearly inhibited. This inhibitory effect was shown at a dose as low as 1 ng/μl, and was maximal at 4 ng/μl (FIG. 8) (p<0.05). Since the hum-Zap, conjugated with saporasin, could only target ribosomes and inhibit their function after internalization at the low concentration, this data confirmed the ability of the Fab to internalize. Another control group treated with Fab alone failed to inhibit the proliferation of A431 cells, ruling out the possibility that the inhibition effect was due to the Fab alone.

The A431 cells were seeded in a 96-well plate at a density of $2\times10^3$/well. After attachment, 50 to 400 ng of hum-Zap (Advanced Targeting System, San Diego, Calif., Cat: #KIT-22-25) with or without the same amount of Fab was added to each well, and the plates were incubated at 37° C. for 24 to 48 hours. Untreated cells were used as controls to calculate the inhibitory effect of cell proliferation. Twenty-four and forty-eight hours after treatment, the viable cell number was measured using the commercial by CellTiter 96 Aqueous Non-Radioactive Cell Proliferation Assay (Promega, G5421).

Example 7

Cytotoxicity of Fab Conjugated Paclitaxel

A431 cells were seeded in 96-well plates (at $2\times10^3$/well) and exposed to different concentrations of Fab conjugated paclitaxel (6.5-52 μM) or paclitaxel alone 48 hours after cell attachment. The cell survival measured by the protocol described above. Untreated cells were also analyzed as controls.

Figure 9:
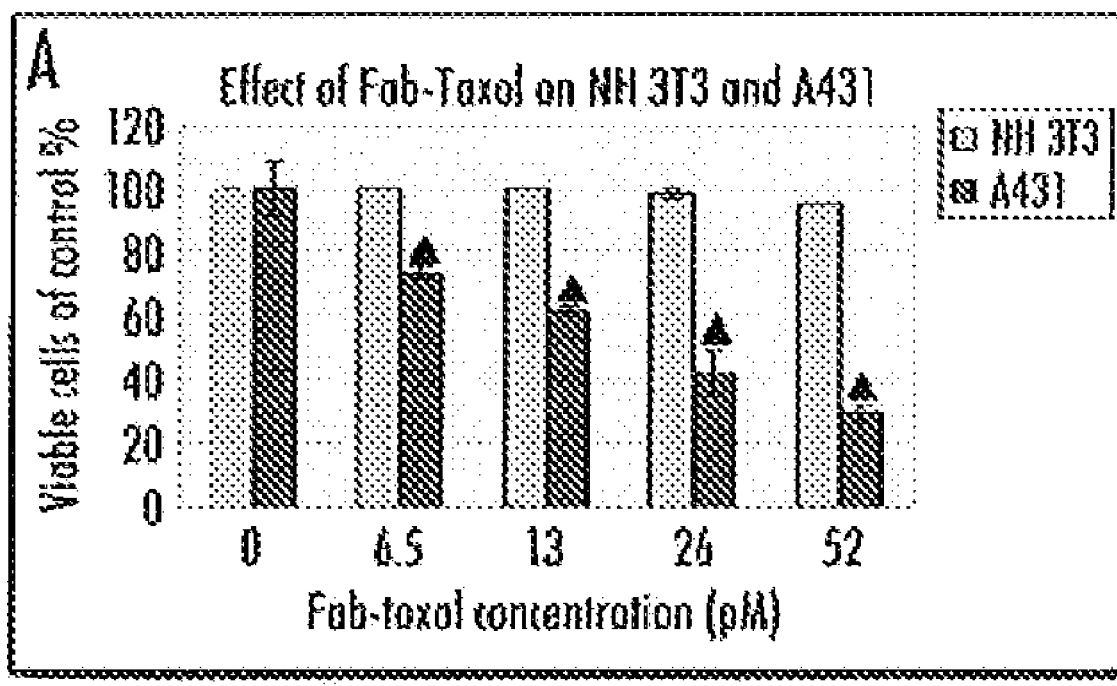
FIG. 9 is a graph showing the effects of different concentrations of Fab-paclitaxel conjugates on A431 cell viability vs. NIH 3T3 cell viability (▲ indicates statistical significance vs. negative control).

The Fab of the present invention (including the $V_L$ and $V_H$ domains shown in SEQ ID NO'S: 3 and 4) were internalized into cells with conjugated paclitaxel and toxicity toward tumor cells was tested. The Fab-paclitaxil conjugate inhibited EGFR-positive A431 cell proliferation and induced apoptosis, with no inhibition of EGFR-negative NIH 3T3 cells (FIG. 9). A431 cell proliferation was inhibited by the Fab-paclitaxel conjugate in a dose-dependent manner. Each concentration was tested in triplicate (p<0.05). The Fab-paclitaxel conjugate was effective at inhibiting A431 cell proliferation at concentrations as low as 6.5 pM. The $IC_{50}$ of A431 cells to paclitaxel alone is about 90 pM (Ojima, supra), and with the present Fab-paclitaxil conjugate, the $IC_{50}$ was 20 pM, four-to-five fold more potent than paclitaxel alone.

Example 8

Apoptosis of Tumor Cells

Low concentrations of paclitaxel can induce apoptosis in breast cancer cell lines, while high concentrations lead to necrosis (Yeung T K et al., supra). TUNEL assays were used to test whether low concentrations of paclitaxel could induce apoptosis of A431 cells.

After treatment with (or without) 26 pM Fab-paclitaxel for 48 hours in 96-well plates, the cells were fixed with 4% paraformaldehyde in PBS for 1 hour at room temperature. Each well was then washed twice with PBS, followed by permeabilization with 0.01% Triton X-100, 0.01% sodium citrate for 5 minutes on ice. After two washes with PBS, the wells were blocked with 5% milk-PBS for 1 hour at 37° C. The TUNEL assay was performed by adding to each well the reaction mixture of an in situ cell death detection kit (Roche, Cat#: 11684795001) at 37° C. for 1 hour in dark. The wells were again washed twice with PBS. Apoptosis was observed under a fluorescence microscope at an excitation wavelength of 488 nm.

Figure 10:
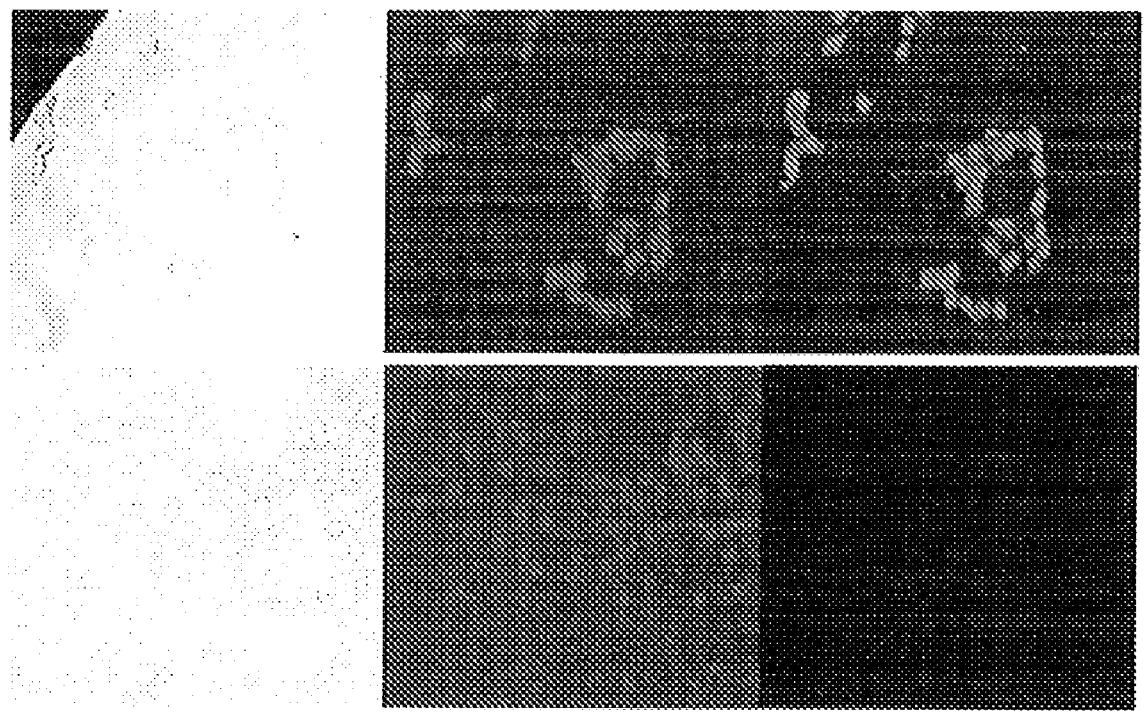
FIG. 10 is a series of micrographs showing apoptosis of A431 cells (TUNEL assay) treated with or without the EGFR Fab conjugated to paclitaxel.

Indeed, apoptosis was observed after 48 hours of exposure to the 26 pM concentration of the conjugate. DNA fragments labeled with fluorescent dUTP at their 3' ends gave a strong signal under fluorescence microscopy at the same location as the DAPI staining in the nucleus, further confirming the underlying apoptosis. However, control cells displayed only a background fluorescence (FIG. 10). The upper panels of FIG. 10 show results of A431 cells treated with 26 pM Fab-paclitaxel conjugates (for 48 hours); and the lower panels show results with untreated A431 cells. (From left: under light microscope, DAPI staining, and TUNEL assay).

Having now fully described this invention, it will be appreciated by those skilled in the art that based upon the teachings herein, the same can be performed within a wide range of equivalent parameters, concentrations, and conditions with- out departing from the spirit and scope of the invention and without undue experimentation. Thus, changes and modifications may be made without departing from this subject matter described herein and its broader aspects and, therefore, the appended claims are to encompass within their scope all such changes and modifications as are within the true spirit and scope of this subject matter described herein.

It will be understood by those skilled in the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

---

What is claimed is:

1. An antibody Fab fragment that binds to epidermal growth factor receptor (EGFR), which fragment is produced by the bacterial strain deposited in the American Type Culture Collection under Patent Deposit Designation ATCC PTA-7830.

2. An antigen-binding antibody fragment that binds to the same epitope or epitopes of EGFR as does the Fab fragment of claim 1.

3. The antibody fragment of claim 1 conjugated to a detectable label or imaging agent.

4. The antibody fragment of claim 1 conjugated to a drug.

5. The antibody fragment of claim 4 wherein said drug is paclitaxel.

6. An antibody Fab fragment that binds specifically to EGFR, characterized by an immunoglobulin heavy (H) chain portion of the Fab, which consists of a $V_H$ domain and a $C_H1$ domain, and an immunoglobulin light (L) chain portion of the Fab, which consists of a $V_L$ domain and a CL domain, wherein the $V_L$ domain is SEQ ID NO:3 and the $V_H$ domain is SEQ ID NO:4;
   or a functional derivative of said Fab fragment that binds to EGFR, wherein said derivative is
      a deletion variant of said Fab fragment in which part or all of the $C_H1$ or $C_L$ domain is deleted.

7. The Fab fragment of claim 6 produced by the *E. coli* strain deposited in the American Type Culture Collection under Patent Deposit Designation ATCC PTA-7830.

8. The Fab fragment or derivative of claim 6 conjugated to a detectable label or imaging agent.

9. The Fab fragment or derivative of claim 6 conjugated to a drug.

10. The Fab fragment or derivative of claim 9 wherein said drug is a cancer chemotherapeutic drug.

11. The Fab fragment or derivative of claim 10 wherein said drug is paclitaxel.

12. The antibody fragment of claim 2 conjugated to a detectable label or imaging agent.

13. The antibody fragment of claim 2 conjugated to a drug.

14. The antibody fragment of claim 13 wherein said drug is paclitaxel.

15. A method for inhibiting growth or proliferation of cells that express EGFRs, comprising contacting said cells with the antibody fragment of claim 2.

16. The method of claim 15 wherein a drug is conjugated to said antibody fragment.

17. The method of claim 15 wherein a drug is a cancer chemotherapeutic drug.

18. The method of claim 17 wherein said drug is paclitaxel.

19. The method according to claim 15, wherein the cells are tumor or cancer cells.

20. A method for inhibiting growth or metastasis of EGFR-expressing tumor or cancer cells in a subject comprising administering to the subject an effective amount of an antibody fragment according to claim 2 conjugated to an anti-cancer agent.

21. The method of claim 20 wherein the anti-cancer agent is a chemotherapeutic drug.

22. The method of claim 21 wherein said drug is paclitaxel.

23. A method for diagnosing EGFR-expressing tumor or cancer in a subject, comprising administering to a subject suspected of having said tumor or cancer an antibody fragment according to claim 2 that is detectably labeled with an imaging agent, wherein detection of the imaging agent in or on cells or in a tissue is diagnostic of said tumor or cancer.

24. A method for detecting the presence of abnormal cells or tissues in a subject in which the amount or level of EGFR expression is abnormally high compared to a known control amount or level of EGFR in normal cells or tissues, the method comprising:
  (a) administering to the subject the antibody fragment of claim 12;
  (b) measuring the binding of said antibody fragment to cells or tissue of the subject by measuring the amount or level of the label or imaging agent to determine the EGFR amount or level;
  (c) comparing the amount or level of EGFR measured in step (b) to said known control amount or level;
wherein, when a higher amount or level measured in step (b) compared to said control amount or level is indicative of the presence of said abnormal cells or tissues in the subject.

25. The method of claim 24 wherein said abnormal cells are tumor or cancer cells or said abnormal tissue is tumor or cancer tissue.

26. A method for enhancing the response of a subject with an EGFR-expressing tumor or cancer to a chemotherapeutic drug directed to said tumor or cancer, comprising administering to said subject an effective amount of the drug-conjugated antibody fragment of claim 13 wherein the drug-conjugated antibody fragment is one that is internalized by cells of said tumor or cancer, wherein, binding of said drug-conjugated antibody fragment to said tumor or cancer cells results in internalization of said drug-conjugated antibody fragment, leading to enhanced response of said subject to said drug compared to administration of said drug alone.

27. A kit useful in a method of diagnosis of an EGFR-expressing tumor or cancer in a subject, comprising a container containing the antibody fragment of claim 12.

28. The kit of claim 27, further comprising one or more containers containing additional agents useful in said diagnostic method and instructions for performance of the method.

29. A kit useful in a method of treatment of an EGFR-expressing tumor or cancer in a subject, comprising a container containing the drug-conjugated antibody fragment of claim 13.

30. The kit of claim 29, further comprising one or more containers containing additional agents useful in said treatment method and instructions for performance of the method.

31. A pharmaceutical or diagnostic composition comprising the antibody fragment of claim 1.

32. The composition of claim 31, wherein the antibody fragment is conjugated to a detectable label or imaging agent.

33. The composition of claim 31, wherein the antibody fragment is conjugated to a drug.

34. A pharmaceutical or diagnostic composition comprising the antibody fragment of claim 2.

35. The composition of claim 34, wherein the antibody fragment is conjugated to a detectable label or imaging agent.

36. The composition of claim 34, wherein the antibody fragment is conjugated to a drug.

37. A pharmaceutical or diagnostic composition comprising the Fab fragment or derivative of claim 6.

38. A kit, comprising a container containing the composition of claim 34.

39. A method for inhibiting growth, proliferation, or metastasis of cells that express EGFRs, comprising contacting said cells with the composition of claim 34.

40. The method of claim 39 wherein a drug is conjugated to said antibody fragment.

41. A method for enhancing the response of a subject with an EGFR- expressing tumor or cancer to a chemotherapeutic drug directed to said tumor or cancer, comprising administering to said subject an effective amount of the composition of claim 36 wherein the antibody fragment is one that is internalized by cells of said tumor or cancer, wherein binding of said drug-conjugated antibody fragment to said tumor or cancer cells results in internalization of said drug-conjugated antibody fragment, leading to enhanced response of said subject to said drug compared to administration of said drug alone.

42. A method for diagnosing EGFR-expressing tumor or cancer in a subject, comprising administering to a subject suspected of having said tumor or cancer the composition according to claim 34 that is detectably labeled with an imaging agent, wherein detection of the imaging agent in or on cells or in a tissue is diagnostic of said tumor or cancer.

* * * * *

UNITED STATES PATENT AND TRADEMARK OFFICE
CERTIFICATE OF CORRECTION

| | |
|---|---|
| PATENT NO. | : 7,790,164 B2 |
| APPLICATION NO. | : 11/940322 |
| DATED | : September 7, 2010 |
| INVENTOR(S) | : Boliang Cao |

It is certified that error appears in the above-identified patent and that said Letters Patent is hereby corrected as shown below:

Column 1
Line 13, "clear—molecules" should be -- clear molecules --.
Lines 34-35, "lysosome Schrama" should be -- lysosome (Schrama --.
Lines 55-56, "antibody) or" should be -- antibody or --.

Column 2
Line 39, "(2005)) Schrama" should be -- (2005) Schrama --.
Line 55, "that is" should be -- that it is --.
Line 60, "Schrama D, et al., supra" should be -- (Schrama D, et al., supra.) --.

Column 3
Lines 1-2, "comprise a human" should be -- comprise human --.
Line 18, "Bio panning" should be -- Bio-panning --.
Lines 25 and 31, "an Fab" should be -- a Fab --.
Line 31, "2006." should be -- 2006). --.
Lines 35-37, ""anti-EGFR' ... Fab'" should be -- anti-EGFR" ... Fab" --.
Line 64, "The can" should be -- It can --.
Line 66, "formulate" should be -- formulated --.

Column 4
Line 2, "of VL the" should be -- of the VL --.
Lines 63 and 64, "subject an. . .is (i) is internalized" should be -- subject in an. . .is (i) internalized. --.

Column 5
Line 16, "cytometry" should be -- cytometry. --.
Lines 58-60, "1994))], . . . fCohgan . . . (1994." should be -- 1994)], Cohgan . . . (1994). --.

Signed and Sealed this
Twelfth Day of July, 2011

David J. Kappos
*Director of the United States Patent and Trademark Office*

Column 6
Line 17, "markers" should be -- marker --.
Line 22, "used in herein" should be -- used herein --.

Column 7
Line 3, "aer" should be -- are --.
Line 59, "(see" should be -- (See --.
Line 63, "an Fab" should be -- a Fab --.

Column 8
Line 5, "manipulation, of" should be -- manipulation of --.
Line 10, "an nucleic" should be -- a nucleic --.
Line 60, after "true" delete "when the".

Column 9
Line 8, "that number" should be -- that the number --.
Line 32, "anti human" should be -- anti-human --.
Line 49, "NIH 3T3" should be -- NIH-3T3 --.
Line 56, "inventors" should be -- inventor --.

Column 10
Line 9, "phase" should be -- phage --.
Line 12, "phase" should be -- phage --.
Line 18, "anti human" should be -- anti-human --.
Line 40, "(2004)0." should be -- (2004). --.
Line 46, "9Yeung" should be -- (Yeung --.
Line 53, "multi drug" should be -- multi-drug --.
Line 55, "(2002)." should be -- (2002)). --.
Lines 57, "anti EGFR" should be -- anti-EGFR --.
Lines 58-59, "Ojima . . . (2002)." should be -- (Ojima . . . (2002).) --.
Lines 59-60, "can not" should be -- cannot --.
Line 65, "anti EGFR" should be -- anti-EGFR --.

Column 11
Line 4, "at a very" should be -- at very --.
Line 10, "are" should be -- is --.
Line 19, "An Fab" should be -- A Fab --.
Line 23, "$V_L$-$C_L$The Fab" should be -- $V_L$-$C_L$. The Fab --.
Lines 32-33, "complementarity determining" should be -- complementarity-determining --.
Line 41, "complimentary the" should be -- complimentary to the --.
Line 55, "2n ed." should be -- 2d ed. --.

Column 12
Line 26, "affinity an" should be -- affinity of an --.
Line 37, "herein" should be -- herein. --.

Column 13
Line 3, "antibody Alterations" should be -- antibody. Alterations --.
Lines 22-23, "NO 3 and H chain . . . NO 4." should be -- NO:3 and the H chain . . . NO:4. --.

Column 14
Lines 2-4, "See . . . 1996)." should be -- (See . . . 1996.) --.
Line 12, "Green. derivatives" should be -- Green derivatives --.
Line 18, "Red. derivatives" should be -- Red derivatives --.
Line 26, "(1998)," should be -- (1998)), --.

Column 15
Line 41, after "suspensions" delete ", solid forms".

Column 16
Line 30, "compriseone" should be -- comprise one --.

Column 17
Line 20, "a least" should be -- at least --.
Line 55, "is (i) is internalized" should be -- is (i) internalized --.

Column 18
Line 31, after "about" delete "a".
Line 52, after "the" delete "by".
Line 64, "450%" should be -- 450µl --.

Column 19
Line 32, "tween-PBS" should be -- Tween-PBS --.
Line 35, "tween-PBS" should be -- Tween-PBS --.
Line 40, after "(Pierce" delete "(??)".
Line 44, "Inc.)" should be -- Inc.). --.
Line 67, after "significant" insert -- . --.

Column 20
Line 5, "'FACS')" should be -- "FACS" --.
Line 20, "anti human" should be -- anti-human --.
Line 45, after "4°C" delete "and".
Line 61, "enlarged)" should be -- enlarged.) --.

Column 21
Line 1, "anti human" should be -- anti-human --.
Lines 11 and 12, "antigengave . . . an Fab" should be -- antigen gave . . . a Fab --.
Line 13, "an Fab" should be -- a Fab --.
Line 42, "(Ka$_{ff}$)" should be -- (K$_{aff}$) --.
Line 53, "cells'" should be -- cells --.

CERTIFICATE OF CORRECTION (continued)
U.S. Pat. No. 7,790,164 B2

Column 22
Line 3, after "commercial" delete "by".
Line 12, "6.5-52 μM" should be -- 6.5-52 pM --.
Line 13, "survival measured" should be -- survival was measured --.
Line 17, "NO'S" should be -- NOS --.
Line 63, "assay)." should be -- assay.) --.

Column 25
Claim 6, Line 53, "CL" should be -- $C_L$ --.

SEQUENCE LISTING

<160> NUMBER OF SEQ ID NOS: 4

<210> SEQ ID NO 1
<211> LENGTH: 318
<212> TYPE: DNA
<213> ORGANISM: homo sapiens

<400> SEQUENCE: 1

```
gccctgactc agcctccctc cgtgtcagtg gccccaggaa agacggccag gattacctgt    60
gggggaaaca acattggaag taaaagtgtg cactggtacc agcagaagcc aggccaggcc   120
cctgtgctgg tcatctatta tgatagcgac cggccctcag ggatccctga gcgattctct   180
ggctccaact ctgggaacac ggccaccctg accatcagca gggtcgaagc cggggatgag   240
gccgactact actgtcaggt gtgggatagt agtagtgatc atccggtgtt cggcggaggg   300
accaagctga ccgtccta                                                  318
```

<210> SEQ ID NO 2
<211> LENGTH: 351
<212> TYPE: DNA
<213> ORGANISM: homo sapiens

<400> SEQUENCE: 2

```
gaggtgcagc tggtggagtc tgggggaggc ttggtacagc ctggcaggtc cctgagactc    60
tcctgtgcag cctctggatt caccttgat gattatgcca tgcactgggt ccggcaagct    120
ccaggcaagg ggctggagtg ggtggcagtt atatggtatg atggaagtaa taatactat   180 gcagactccg tgaagggccg attcaccatc tccagagaca attccaagaa cacgctgtat   240
ctgcaaatga acagcctgag agccgaggac acggctgtgt attactgtgc gaggactcta   300
tacagtaaca ttgactactg gggccagggc accctggtca ccgtctcctc t           351
```

<210> SEQ ID NO 3
<211> LENGTH: 106
<212> TYPE: PRT
<213> ORGANISM: homo sapiens

<400> SEQUENCE: 3

```
Ala Leu Thr Gln Pro Pro Ser Val Ser Val Ala Pro Gly Lys Thr Ala
  1               5                  10                  15

Arg Ile Thr Cys Gly Gly Asn Asn Ile Gly Ser Lys Ser Val His Trp
                 20                  25                  30

Tyr Gln Gln Lys Pro Gly Gln Ala Pro Val Leu Val Ile Tyr Tyr Asp
             35                  40                  45

Ser Asp Arg Pro Ser Gly Ile Pro Glu Arg Phe Ser Gly Ser Asn Ser
         50                  55                  60

Gly Asn Thr Ala Thr Leu Thr Ile Ser Arg Val Glu Ala Gly Asp Glu
 65                  70                  75                  80

Ala Asp Tyr Tyr Cys Gln Val Trp Asp Ser Ser Ser Asp His Pro Val
                 85                  90                  95
```

-continued

```
Phe Gly Gly Gly Thr Lys Leu Thr Val Leu
            100                 105

<210> SEQ ID NO 4
<211> LENGTH: 117
<212> TYPE: PRT
<213> ORGANISM: Homo sapiens

<400> SEQUENCE: 4

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Leu Tyr Ser Asn Ile Asp Tyr Trp Gly Gln Gly Thr Leu
            100                 105                 110

Val Thr Val Ser Ser
            115
```